(12) United States Patent
Camire et al.

(10) Patent No.: US 8,557,762 B2
(45) Date of Patent: Oct. 15, 2013

(54) SNAKE FACTOR V AND METHODS OF USE THEREOF AS A PROCOAGULANT

(75) Inventors: Rodney Camire, Sicklerville, NJ (US); Mettine H. A. Bos, Amsterdam (NL)

(73) Assignee: The Children's Hospital of Philadelphia, Philadelphia, PA (US)

( * ) Notice: Subject to any disclaimer, the term of this patent is extended or adjusted under 35 U.S.C. 154(b) by 89 days.

(21) Appl. No.: 13/130,378

(22) PCT Filed: Nov. 23, 2009

(86) PCT No.: PCT/US2009/065515
§ 371 (c)(1),
(2), (4) Date: Jul. 20, 2011

(87) PCT Pub. No.: WO2010/060035
PCT Pub. Date: May 27, 2010

(65) Prior Publication Data
US 2011/0268790 A1    Nov. 3, 2011

Related U.S. Application Data

(60) Provisional application No. 61/116,913, filed on Nov. 21, 2008.

(51) Int. Cl.
*C07K 14/00* (2006.01)
*C07H 21/02* (2006.01)
*C12N 15/00* (2006.01)

(52) U.S. Cl.
USPC .......................... 514/1; 536/23.1; 435/320.1

(58) Field of Classification Search
USPC ............ 514/1; 536/23.1; 435/320.1; 530/350
See application file for complete search history.

(56) References Cited

U.S. PATENT DOCUMENTS

2003/0143759 A1    7/2003   Dahlback

FOREIGN PATENT DOCUMENTS

WO    2007/101106    9/2007
WO    2009/079690    7/2009

OTHER PUBLICATIONS

Bos, M.H., et al. "Venom factor V from the common brown snake escapes hemostatic regulation through procoagulant adaptations." Blood. Jul. 16, 2009;114(3):686-92. Epub Apr. 13, 2009.
Rao, V.S., et al. "The nonenzymatic subunit of pseutarin C, a prothrombin activator from eastern brown snake (*Pseudonaja textilis*) venom, shows structural similarity to mammalian coagulation factor V." Blood. Aug. 15, 2003;102 (4):1347-54. Epub May 1, 2003.
GenBank Accession #AY168281, [online]: downloaded from http://www.ncbi.nlm.nih.gov/nuccore/33578333 on Mar. 14, 2010.

*Primary Examiner* — Karen Cochrane Carlson
(74) *Attorney, Agent, or Firm* — Dann, Dorfman, Herrell & Skillman; Kathleen D. Rigaut

(57) ABSTRACT

Compositions and Methods for the treatment of coagulation disorders using Factor V variants are provided. Preferred disorders include hemophilia A and B.

13 Claims, 9 Drawing Sheets

>FV-PTextilis + SP (1bp - 4374bp, direct) 4374bp (SEQ ID NO: 1)
ATGTTCCCAGGCTGCCCACGCCTCTGGGTCCTGGTGGTCTTGGGCACCAGCTGGGTAGGCTGGGGGAGCC
AAGGGACAGAAGCGGCTCAGCTCAGGGAGTACCATATAGCTGCTCAGCTGGAAGACTGGGATTACAACCC
CCAACCTGAGGAGCTATCCAGATTATCAGAGTCAGATCTTACGTTTAAAAAAATTGTCTATAGAGAATAT
GAACTAGATTTCAAACAAGAGAAGCCAAGAGATGCGCTCTCAGGGCTCCTAGGGCCAACACTACGTGGAG
AAGTGGGAGACAGCCTCATAATTTATTTCAAGAATTTTGCTACTCAGCCTGTGAGCATTCACCCGCAGAG
TGCCGTGTACAACAAATGGTCAGAAGGTTCTTCATATTCTGATGGAACATCAGATGTGGAAAGACTGGAT
GATGCTGTGCCTCCAGGCCAGTCGTTCAAGTATGTGTGGAATATCACTGCAGAAATTGGGCCAAAGAAAG
CTGATCCTCCCTGTCTCACTTATGCGTACTACTCACATGTAAACATGGTGCGAGACTTTAATTCTGGTCT
CATTGGTGCTTTGCTGATATGTAAAGAAGGAAGCCTGAATGCAAATGGTTCACAAAAATTCTTCAACAGA
GAATATGTGCTGATGTTTTCTGTGTTTGATGAAAGCAAGAACTGGTACAGAAAGCCCTCACTACAGTACA
CAATTAATGGGTTTGCCAATGGAACATTGCCTGATGTTCAGGCTTGTGCTTATGATCATATTAGCTGGCA
TTTGATAGGAATGAGTTCCAGTCCTGAGATCTTCTCTGTTCACTTCAATGGACAAACCTTGGAACAAAAC
CATTACAAAGTGTCAACCATCAACCTTGTCGGAGGTGCCTCAGTAACAGCCGACATGTCAGTGAGCAGGA
CAGGAAAATGGCTAATATCTTCTCTGGTTGCAAAGCATCTACAAGCTGGGATGTATGGTTATCTAAATAT
CAAAGACTGTGGAAATCCAGATACTTTAACAAGAAAGTTATCCTTTAGAGAACTGATGAAGATTAAGAAC
TGGGAATATTTCATTGCTGCAGAAGAAATCACCTGGGATTATGCTCCAGAAATTCCTAGCAGTGTTGACA
GAAGATACAAAGCTCAGTATCTGGATAATTTTTCAAATTTTATTGGCAAGAAATACAAAAAGGCAGTTTT
CAGGCAATATGAAGACGGCAATTTCACTAAACCGACCTATGCCATTTGGCCCAAAGAACGTGGAATTCTG
GGCCCCGTTATCAAAGCTAAAGTCAGAGACACAGTAACAATTGTATTCAAAAATCTGGCCAGTCGACCTT
ACAGCATTTATGTGCATGGAGTTTCCGTTTCAAAAGATGCAGAAGGAGCTATTTATCCTTCAGATCCCAA
AGAGAATATAACTCATGGCAAAGCAGTTGAACCAGGACAGGTCTACACATATAAATGGACTGTGCTGGAT
ACAGATGAACCTACAGTAAAGGATTCTGAGTGCATTACTAAATTATATCATAGTGCTGTGGACATGACAA
GAGATATTGCTTCAGGACTTATTGGGCCACTTCTGGTTTGTAAACACAAGGCACTCAGCGTCAAGGGGGT
ACAGAATAAAGCTGATGTGGAACAGCATGCAGTCTTCGCAGTGTTTGATGAAAACAAGAGCTGGTACTTG
GAAGACAATATCAAGAAATACTGCAGCAATCCTTCCGCTGTTAAGAAAGATGACCCTAAATTTTACAAGT
CCAATGTTATGTACACACTCAATGGCTATGCATCAGATAGAACAGAGGTTTTGAGGTTTCATCAGTCTGA
AGTTGTTCAATGGCACCTCACCAGCGTAGGTACAGTGGATGAGATTGTTCCAGTACATCTTTCTGGTCAC
ACCTTCTTATCCAAGGGAAAACATCAAGATATTTTAAATCTTTTCCCCATGAGTGGTGAATCTGCTACTG
TAACAATGGACAATCTAGGAACCTGGCTTCTGTCATCATGGGGCTCCTGTGAGATGAGCAATGGCATGAG
ATTGAGATTTTGGATGCCAATTATGATGATGAAGATGAGGGAAATGAAGAAGAGGAAGAAGATGATGGT
GATATTTTGCCGACATTTTCATTCCTTCAGAAGTAGTAAAAAAGAAAGAAGAGGTTCCCGTAAATTTTG
TACCAGACCCAGAATCGGATGCGCTAGCAAAAGAATTAGGATTAATAGATGACGAGGGTAATCCAATAAT
ACAGCCACGCAGGGAACAGACAGAGGATGATGAAGAACAGCTAATGAAAGCTTCAATGCTTGGGCTTCGA
TCATTTAAGGGGTCAGTTGCTGAAGAAGAATTGAAACACACAGCTCTAGCTTTAGAAGAAGATGCCCATG
CTTCTGATCCTCGAATTGACAGTAATAGTGCACGTAATCCTGACGACATAGCTGGACGCTACCTGCGTAC
TATCAACCGTGGAAATAAAAGGAGGTACTACATTGCAGCAGAAGAAGTTTTGTGGGACTACTCACCGATC
GGAAAAAGTCAAGTGAGAAGTCGCGCAGCCAAGACCACATTCAAAAAAGCTATTTTCCGAAGTTATCTTG
ATGATACTTTCCAGACACCTAGCACTGGAGGAGAATATGAAAAGCATCTTGGTATACTGGGTCCTATCAT
TAGGGCTGAGGTGGATGATGTAATCGAAATTCAGTTCAAAAATTTGGCCTCTAGACCATACTCACTTCAT
GCTCATGGCCTTCTCTATGAGAAATCTTCTGAAGGCAGAAGCTATGATGACAAGTCTCCTGAATTGTTCA
AAAAGGATGATGCTATCATGCCAAATGGCACATACACATATGTCTGGCAAGTCCCTCCACGGTCAGGACC
AACAGACAATACAGAAAAATGTAAATCATGGGCCTATTACTCTGGTGTAAATCCGGAAAAAGATATTCAC
TCTGGCTTAATTGGACCTATTTTGATCTGCCAGAAAGGCATGATTGACAAGTACAACAGGACAATAGACA
TAAGGGAATTTGTCTTGTTTTTTATGGTCTTTGATGAGGAGAAAAGCTGGTACTTTCCAAAATCTGACAA
AAGCACTTGTGAAGAGAAACTTATAGGAGTCCAATCTCTCCACACATTTCCTGCAATTAATGGGATCCCT
TATCAGCTGCAAGGCTTGACGATGTACAAAGATGAGAATGTCCACTGGCATTTGCTGAACATGGGTGGGC
CCAAAGATATCCATGTTGTTAATTTTCATGGTCAGACATTCACTGAAGAGGGAAGGGAAGATAATCAACT
TGGAGTCCTTCCTCTTCTTCCTGGTACATTCGCCTCCATCAAAATGAAACCATCCAAAATTGGCACATGG
CTTTTAGAAACAGAAGTTGGTGAAAATCAGGAAAGAGGAATGCAGGCTCTCTTTACTGTCATTGACAAAG
ATTGTAAATTACCAATGGGACTGGCAAGTGGGATAATACAAGACTCACAGATCAGTGCTTCAGGTCATGT
TGGATATTGGGAGCCCTAAGCTAGCAAGACTGAATAATACTGGAAAATATAATGCTTGGAGCATCATAAAG

Fig. 5B

```
AAGGAACATGAACATCCGTGGATCCAGATAGACCTACAAAGACAAGTTGTCATCACAGGCATTCAGACCC
AAGGAACCGTGCAACTACTGCAACATTCGTATACTGTGGAATATTTTGTTACCTACAGCGAAGATGGGCA
AAACTGGATTACTTTTAAAGGAAGACATTCCGAAACACAAATGCATTTTGAGGGTAATTCAGATGGCACC
ACAGTAAAAGAAAACCACATTGATCCTCCTATTATTGCCAGATATATTAGGCTGCATCCAACCAAGTTCT
ACAACAGACCTACTTTCCGCATTGAACTGTTAGGTTGTGAAGTTGAAGGTTGCTCAGTGCCATTGGGAAT
GGAAAGTGGGGCTATCAAGAATTCAGAGATTACAGCCTCTTCTTATAAGAAGACTTGGTGGAGTTCATGG
GAACCATTCCTTGCACGACTCAATCTGGAAGGAGGAACAAATGCTTGGCAACCAGAGGTAAACAACAAAG
ATCAATGGTTACAAATTGACCTGCAACACCTTACAAAAATAACAAGCATAATAACTCAAGGAGCCACATC
AATGACTACATCAATGTATGTGAAAACATTCTCCATCCATTATACTGATGACAATTCAACATGGAAGCCT
TATTTGGATGTTCGCACTTCCATGGAAAAGGTTTTCACAGGAAATATTAACAGTGATGGTCATGTCAAAC
ATTTTTTCAAACCCCCTATATTGTCCAGGTTCATTCGTATCATCCCTAAAACATGGAATCAATATATTGC
ACTCCGGATAGAATTGTTTGGTTGTGAAGTTTTT
```

Fig. 5C

>(1bp - 4374bp, direct) (SEQ ID NO: 2)
ATGTTCCCCGGCTGCCCCCGCCTGTGGGTGCTGGTGGTGCTGGGCACCAGCTGGGTGGGCTGGGGCAG
CCAGGGCACCGAGGCCGCCCAGCTGCGCGAGTACCACATCGCCGCCCAGCTGGAGGACTGGGACTACA
ACCCCCAGCCCGAGGAGCTGAGCCGCCTGAGCGAGAGCGACCTGACCTTCAAGAAGATCGTGTACCGC
GAGTACGAGCTGGACTTCAAGCAGGAGAAGCCCCGCGACGCCCTGAGCGGCCTGCTGGGCCCCACCCT
GCGCGGCGAGGTGGGCGACAGCCTGATCATCTACTTCAAGAACTTCGCCACCCAGCCCGTGAGCATCC
ACCCCCAGAGCGCCGTGTACAACAAGTGGAGCGAGGGCAGCAGCTACAGCGACGGCACCAGCGACGTG
GAGCGCCTGGACGACGCCGTGCCCCCGGCCAGAGCTTCAAGTACGTGTGGAACATCACCGCCGAGAT
CGGCCCCAAGAAGGCCGACCCCCCTGCCTGACCTACGCCTACTACAGCCACGTGAACATGGTGCGCG
ACTTCAACAGCGGCCTGATCGGCGCCCTGCTGATCTGCAAGGAGGGCAGCCTGAACGCCAACGGCAGC
CAGAAGTTCTTCAACCGCGAGTACGTGCTGATGTTCAGCGTGTTCGACGAGAGCAAGAACTGGTACCG
CAAGCCCAGCCTGCAGTACACCATCAACGGCTTCGCCAACGGCACCCTGCCCGACGTGCAGGCCTGCG
CCTACGACCACATCAGCTGGCACCTGATCGGCATGAGCAGCAGCCCCGAGATCTTCAGCGTGCACTTC
AACGGCCAGACCCTGGAGCAGAACCACTACAAGGTGAGCACCATCAACCTGGTGGGCGGCGCCAGCGT
GACCGCCGACATGAGCGTGAGCCGCACCGGCAAGTGGCTGATCAGCAGCCTGGTGGCCAAGCACCTGC
AGGCCGGCATGTACGGCTACCTGAACATCAAGGACTGCGGCAACCCCGACACCCTGACCCGCAAGCTG
AGCTTCGCGAGCTGATGAAGATCAAGAACTGGGAGTACTTCATCGCCGCCGAGGAGATCACCTGGGA
CTACGCCCCCGAGATCCCCAGCAGCGTGGACCGCCGCTACAAGGCCCAGTACCTGGACAACTTCAGCA
ACTTCATCGGCAAGAAGTACAAGAAGGCCGTGTTCCGCCAGTACGAGGACGGCAACTTCACCAAGCCC
ACCTACGCCATCTGGCCCAAGGAGCGCGGCATCCTGGGCCCCGTGATCAAGGCCAAGGTGCGCGACAC
CGTGACCATCGTGTTCAAGAACCTGGCCAGCCGCCCCTACAGCATCTACGTGCACGGCGTGAGCGTGA
GCAAGGACGCCGAGGGCGCCATCTACCCCAGCGACCCCAAGGAGAACATCACCCACGGCAAGGCCGTG
GAGCCCGGCCAGGTGTACACCTACAAGTGGACCGTGCTGGACACCGACGAGCCCACCGTGAAGGACAG
CGAGTGCATCACCAAGCTGTACCACAGCGCCGTGGACATGACCCGCGACATCGCCAGCGGCCTGATCG
GCCCCCTGCTGGTGTGCAAGCACAAGGCCCTGAGCGTGAAGGGCGTGCAGAACAAGGCCGACGTGGAG
CAGCACGCCGTGTTCGCCGTGTTCGACGAGAACAAGAGCTGGTACCTGGAGGACAACATCAAGAAGTA
CTGCAGCAACCCCAGCGCCGTGAAGAAGGACGACCCCAAGTTCTACAAGAGCAACGTGATGTACACCC
TGAACGGCTACGCCAGCGACCGCACCGAGGTGCTGCGCTTCCACCAGAGCGAGGTGGTGCAGTGGCAC
CTGACCAGCGTGGGCACCGTGGACGAGATCGTGCCCGTGCACCTGAGCGGCCACACCTTCCTGAGCAA
GGGCAAGCACCAGGACATCCTGAACCTGTTCCCCATGAGCGGCGAGAGCGCCACCGTGACCATGGACA
ACCTGGGCACCTGGCTGCTGAGCAGCTGGGCAGCTGCGAGATGAGCAACGGCATGCGCCTGCGCTTC
CTGGACGCCAACTACGACGACGAGGACGAGGGCAACGAGGAGGAGGAGGAGGACGACGGCGACATCTT
CGCCGACATCTTCATCCCCAGCGAGGTGGTGAAGAAGAAGGAGGAGGTGCCCGTGAACTTCGTGCCCG
ACCCCGAGAGCGACGCCCTGGCCAAGGAGCTGGGCCTGATCGACGACGAGGGCAACCCCATCATCCAG
CCCCGCCGCGAGCAGACCGAGGACGACGAGGAGCAGCTGATGAAGGCCAGCATGCTGGGCCTGCGCAG
CTTCAAGGGCAGCGTGGCCGAGGAGGAGCTGAAGCACACCGCCCTGGCCCTGGAGGAGGACGCCCACG
CCAGCGACCCCCGCATCGACAGCAACAGCGCCCGCAACCCCGACGACATCGCCGGCCGCTACCTGCGC
ACCATCAACCGCGGCAACAAGCGCCGCTACTACATCGCCGCCGAGGAGGTGCTGTGGGACTACAGCCC
CATCGGCAAGAGCCAGGTGCGCAGCCGCGCCGCCAAGACCACCTTCAAGAAGGCCATCTTCCGCAGCT
ACCTGGACGACACCTTCCAGACCCCCAGCACCGGCGGCGAGTACGAGAAGCACCTGGGCATCCTGGGC
CCCATCATCCGCGCCGAGGTGGACGACGTGATCGAGATCCAGTTCAAGAACCTGGCCAGCCGCCCCTA
CAGCCTGCACGCCCACGGCCTGCTGTACGAGAAGAGCAGCGAGGGCCGCAGCTACGACGACAAGAGCC
CCGAGCTGTTCAAGAAGGACGACGCCATCATGCCCAACGGCACCTACACCTACGTGTGGCAGGTGCCC
CCCCGCAGCGGCCCCACCGACAACACCGAGAAGTGCAAGAGCTGGCCTACTACAGCGGCGTGAACCC
CGAGAAGGACATCCACAGCGGCCTGATCGGCCCCATCCTGATCTGCCAGAAGGGCATGATCGACAAGT
ACAACCGCACCATCGACATCCGCGAGTTCGTGCTGTTCTTCATGGTGTTCGACGAGGAGAAGAGCTGG
TACTTCCCCAAGAGCGACAAGAGCACCTGCGAGGAGAAGCTGATCGGCGTGCAGAGCCTGCACACCTT
CCCCGCCATCAACGGCATCCCCTACCAGCTGCAGGGCCTGACCATGTACAAGGACGAGAACGTGCACT
GGCACCTGCTGAACATGGGCGGCCCCAAGGACATCCACGTGGTGAACTTCCACGGCCAGACCTTCACC
GAGGAGGGCCGCGAGGACAACCAGCTGGGCGTGCTGCCCCTGCTGCCCGGCACCTTCGCCAGCATCAA
GATGAAGCCCAGCAAGATCGGCACCTGGCTGCTGGAGACCGAGGTGGGCGAGAACCAGGAGCGCGGCA
TGCAGGCCCTGTTCACCGTGATCGACAAGGACTGCAAGCTGCCCATGGGCCTGGCCAGCGGCATCATC
CAGGACAGCCAGATCAGCGCCAGCGGCCACGTGGGCTACTGGGAGCCCAAGCTGGCCCGCCTGAACAA
CACCGGCAAGTACAACGCCTGGAGCATCATCAAGAAGGAGCACGAGCACCCCTGGATCCAGATCGACC
TGCAGCGCCAGGTGGTGATCACCGGCATCCAGACCCAGGGCACCGTGCAGCTGCTGCAGCACAGCTAC
ACCGTGGAGTACTTCGTGACCTACAGCGAGGACGGCCAGAACTGGATCACCTTCAAGGGCCGCCACAG
CGAGACCCAGATGCACTTCGAGGGCAACAGCGACGGCACCACCGTGAAGGAGAACCACATCGACCCCC

Fig. 5D

```
CCATCATCGCCCGCTACATCCGCCTGCACCCCACCAAGTTCTACAACCGCCCCACCTTCCGCATCGAG
CTGCTGGGCTGCGAGGTGGAGGGCTGCAGCGTGCCCCTGGGCATGGAGAGCGGCGCCATCAAGAACAG
CGAGATCACCGCCAGCAGCTACAAGAAGACCTGGTGGAGCAGCTGGGAGCCCTTCCTGGCCCGCCTGA
ACCTGGAGGGCGGCACCAACGCCTGGCAGCCCGAGGTGAACAACAAGGACCAGTGGCTGCAGATCGAC
CTGCAGCACCTGACCAAGATCACCAGCATCATCACCCAGGGCGCCACCAGCATGACCACCAGCATGTA
CGTGAAGACCTTCAGCATCCACTACACCGACGACAACAGCACCTGGAAGCCCTACCTGGACGTGCGCA
CCAGCATGGAGAAGGTGTTCACCGGCAACATCAACAGCGACGGCCACGTGAAGCACTTCTTCAAGCCC
CCCATCCTGAGCCGCTTCATCCGCATCATCCCCAAGACCTGGAACCAGTACATCGCCCTGCGCATCGA
GCTGTTCGGCTGCGAGGTGTTC
```

SNAKE FACTOR V AND METHODS OF USE THEREOF AS A PROCOAGULANT

This application is a §371 national phase application of PCT/US2009/065515 filed Nov. 23, 2009, which claims the benefit of priority under 35 U.S.C. §119(e) to U.S. Provisional Patent Application 61/116,913, filed on Nov. 21, 2008. The disclosures of the foregoing application are incorporated by reference in their entirety.

Pursuant to 35 U.S.C. §202(c) it is acknowledged that the U.S. Government has certain rights in the invention described herein, which was made in part with funds from the National Institutes of Health, Grant Number, HL-088010 and P01 HL-74124.

FIELD OF THE INVENTION

The present invention relates the fields of medicine and hematology. More specifically, the invention describes therapeutic strategies using snake venom derived variants of Factor V (FV) and derivatives thereof for modulating the coagulation cascade in patients in need thereof.

BACKGROUND OF THE INVENTION

Several publications and patent documents are cited throughout the specification in order to describe the state of the art to which this invention pertains. Each of these citations is incorporated herein by reference as though set forth in full.

Blood coagulation FV is a multi-domain protein (A1-A2-B-A3-C1-C2) that circulates as a procofactor with little or no procoagulant activity. Conversion to the active cofactor state (FVa) involves proteolytic removal of a large, heavily glycosylated central B-domain mediated by thrombin (1). FVa reversibly associates with the serine protease factor Xa (FXa) on a negatively charged membrane surface in the presence of calcium ions to form prothrombinase, the physiological activator of prothrombin (2). Since FVa greatly enhances thrombin generation (1), maintaining FV as an inactive procofactor undoubtedly plays a critical regulatory role that has likely evolved to maintain normal hemostasis. Recently, it has been shown that discrete sequences within the B-domain contribute to the mechanism by which FV persists as an inactive procofactor (3, 4). Elimination of this region results in FV activation without the need for proteolytic processing.

FV is widely represented across the vertebrate lineage with high homology found between the A and C domains and poor homology between B-domains (5, 6). Recent genomic data show that while the length of the B-domain is generally conserved among mammals (~800 residues), it varies considerably in lower vertebrates (i.e. ~500 residues in *Fugu rubripes*) (5, 6); the functional implications of these structural changes are not understood. A striking example of major alterations to the B-domain comes from a group of Australian land snakes (*Oxyuranus microlepidotus*, *Pseudonaja textilis*, and *Oxyuranus scutellatus*). These species are unique in that, in addition to circulating FV as part of their hemostatic system, they also have FV in their venom. Venom-derived FV from each of these species shares ~44% sequence homology with mammalian FV having a similar domain structure (7-9). However, the B-domain length is dramatically shortened compared to human FV (~46 versus 836 residues). The venom from these snakes is considered the most toxic in the world, is strongly procoagulant and induces, among other symptoms, disseminated intravascular coagulopathy (10). It contains large amounts of FV as well as a FXa-like enzyme, together forming a complex which is a powerful prothrombin activator. This complex from *O. scutellatus* (oscutarin C) and *P. textilis* (pseutarin C) has been partially purified and characterized from crude venom (11-15). Both convert prothrombin to thrombin and their activities are enhanced, to varying degrees, by calcium and phospholipid, but not FVa. Furthermore, pseutarin C also appears resistant to activated protein C (APC), potentially contributing to its role as a potent toxin (7).

SUMMARY OF THE INVENTION

In accordance with the present invention a method for the treatment of a blood coagulation disorder in a patient in need thereof is provided. An exemplary method entails administering an effective amount of an activated form of FV variant or a derivative thereof, thereby enhancing clot formation in said patient and ameliorating the symptoms of the bleeding disorder. In one embodiment the variant factor V is encoded by a nucleic acid having the sequence of SEQ ID NO: 1. In another embodiment, the variant Factor V is encoded by the codon optimized nucleic acid having the sequence of SEQ ID NO: 2.

The method and Factor V pro-coagulant can be used for the treatment of blood coagulation disorders which include, without limitation, hemophilia A and B, hemophilia A and B associated with inhibitory antibodies, coagulation factor deficiency, vitamin K epoxide reductase C1 deficiency, gamma-carboxylase deficiency, bleeding associated with trauma, injury, thrombosis, thrombocytopenia, stroke, coagulopathy, disseminated intravascular coagulation (DIC); over-anticoagulation treatment disorders, Bernard Soulier syndrome, Glanzman thromblastemia, and storage pool deficiency. Alternatively, the blood coagulation disorder may be due to administration of heparin, low molecular weight heparin, pentasaccharide, warfarin, small molecule antithrombotics and FXa inhibitors.

The variant Factor V of the invention may be directly infused or administered topically to a patient or may be delivered in the form of a vector encoding the same.

Also provided is a humanized and improved Factor V variant which exhibits one or more of the following properties: the FV variant is synthesized in an active, cofactor state; the FV variant possesses a unique conformation such as to allow it to bypass the normal requirement for a membrane surface to achieve high affinity binding to its serine protease factor Xa (FXa); and the FV variant is functionally resistant to inactivation by activated protein C (APC), via inclusion of a unique disulfide bond connecting its heavy and light chains.

In another embodiment of the invention, an isolated nucleic acid of SEQ ID NO: 2 encoding snake Factor V is provided. Such nucleic acids can be contained in an expression vector for use.

In yet another embodiment, the invention provides an isolated snake Factor V protein encoded by the nucleic acid of SEQ ID NO: 1. The snake Factor V protein can be contained in a liposome or micelle. Additionally, the invention provides a pharmaceutical composition comprising the snake Factor V protein contained in a pharmaceutically acceptable excipient.

DESCRIPTION OF THE DRAWINGS

FIG. 1. SDS-PAGE analysis of purified proteins. Proteins (3 μg/lane) were subjected to SDS-PAGE under reducing (panels A, C) or non-reducing (panel B) conditions and visualized by staining with Coomassie Brilliant Blue R-250. Lane 1, pt-rFV; lane 2, pt-rFV-QQ; lane 3, pt-rFV plus thrombin; lane 4, pt-rFV-QQ plus thrombin, lane 5, rFX; lane 6, rFXa;

lane 7, pt-FXa. The apparent molecular weights of the standards are indicated on the left. Panels A and B share the same markers. N-terminal sequence results of the indicated protein bands are shown. The dash (-) as position six indicates that the yield was too low to accurately assign an amino acid and likely represents the presence of γ-carboxyglutamic acid.

Figure 2:
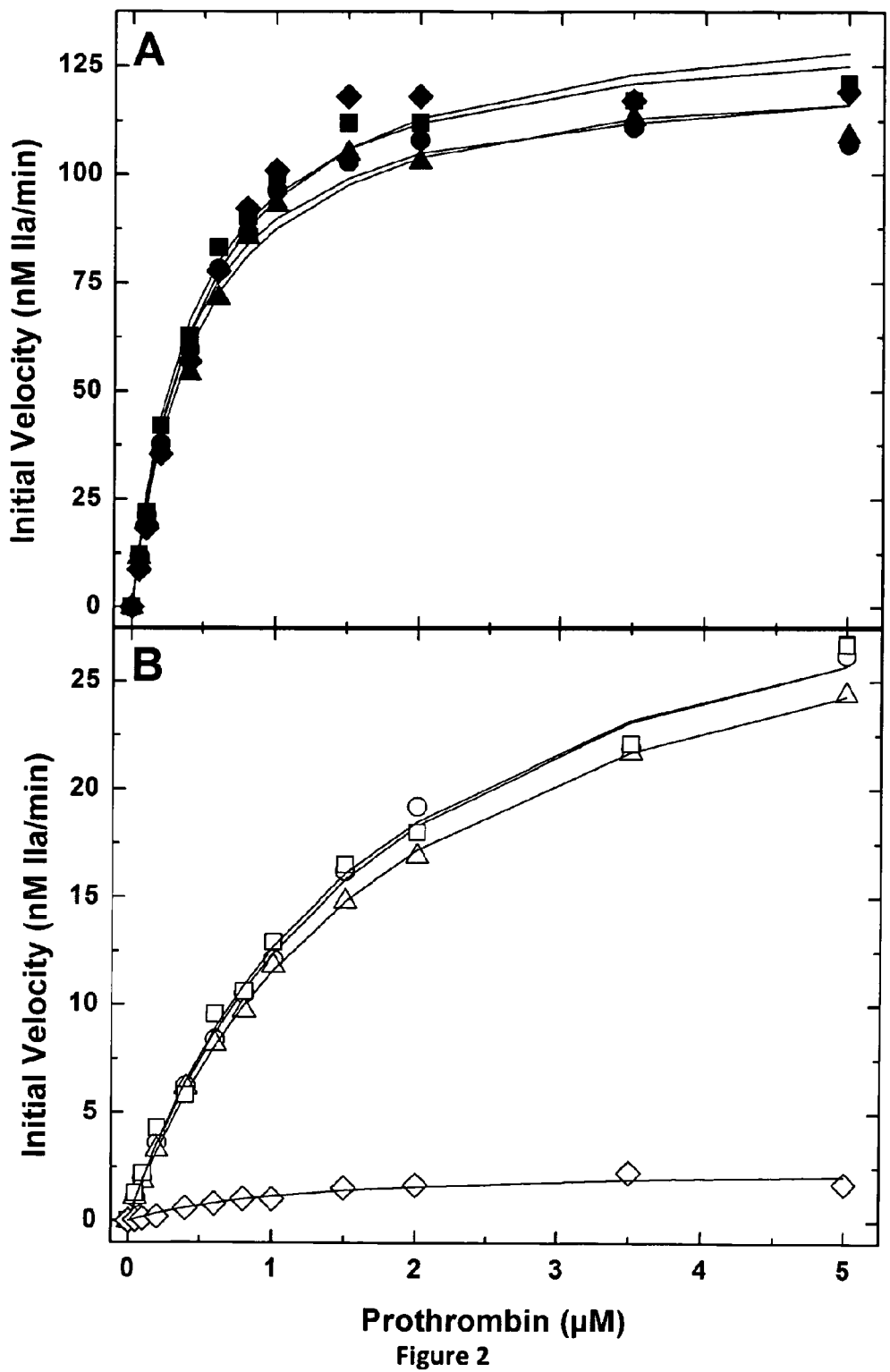

FIG. 2. Determination of kinetic constants for cleavage of prothrombin in the presence or absence of PCPS. The initial velocity of thrombin generation was determined at increasing concentrations of prothrombin in the presence (panel A) or absence (panel B) of 50 μM PCPS and 3 μM DAPA with 0.1 nM pt-FXa and 20 nM hFV-810 (-◆- or -◇-), pt-rFV (-●- or -○-), pt-rFV-QQ (-▲- or -△-), or pt-rFVa (-■- or -□-). The lines were drawn following analysis of all data sets to a rectangular hyperbola, and the fitted kinetic constants can be found in Table 2. The data are representative of two similar experiments.

Figure 3:
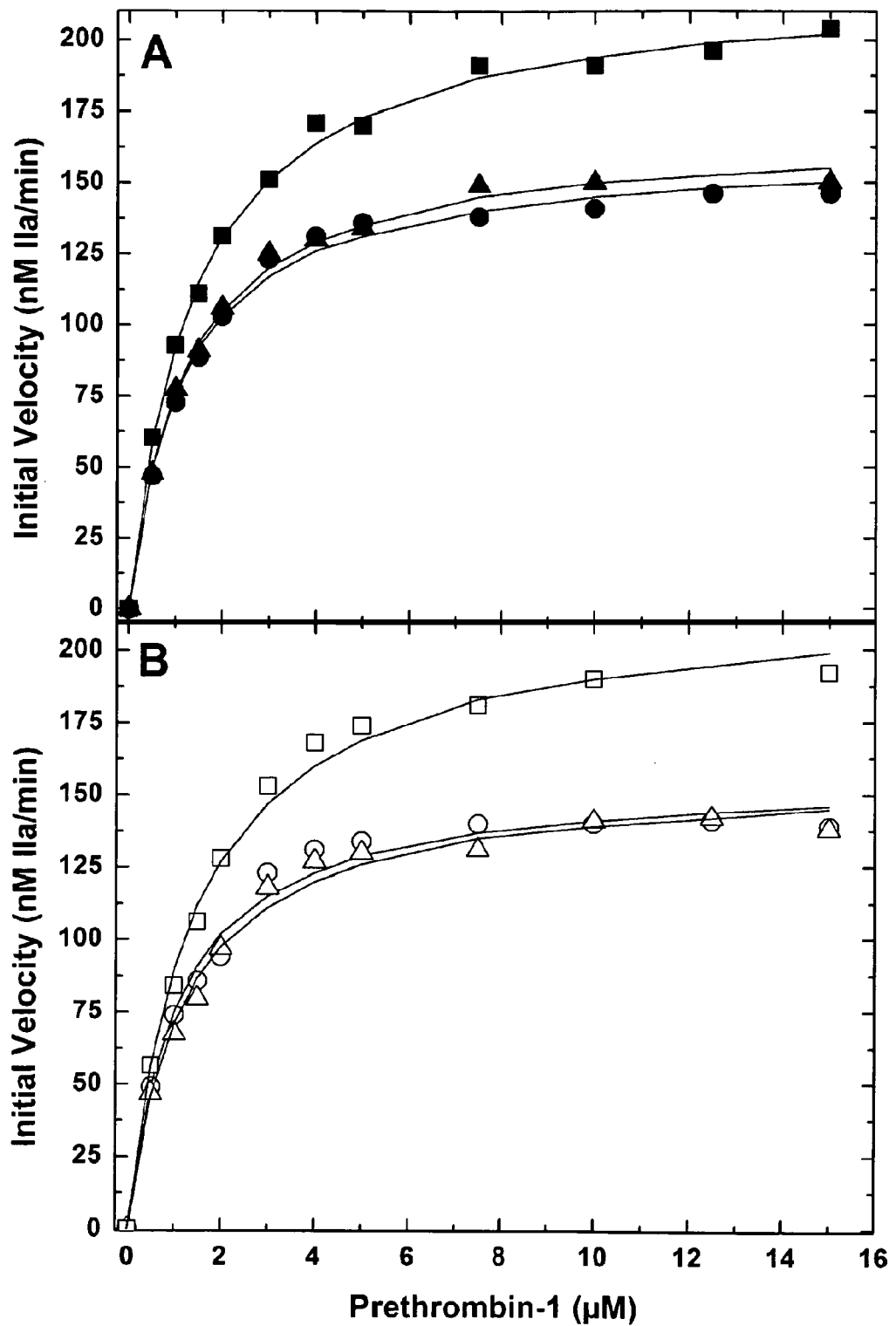

FIG. 3. Determination of kinetic constants for cleavage of prethrombin-1 in the presence or absence of PCPS. The initial velocity of thrombin generation was determined at increasing concentrations of prethrombin-1 in the presence (panel A) or absence (panel B) of 50 μM PCPS and 3 μM DAPA with 0.1 nM pt-FXa and 20 nM pt-rFV (-●- or -○-), pt-rFV-QQ (-▲- or -△-), or pt-rFVa (-■- or -□-). The lines were drawn following analysis of all data sets to a rectangular hyperbola, and the fitted kinetic constants can be found in Table 2. The data are representative of two similar experiments.

Figure 4:
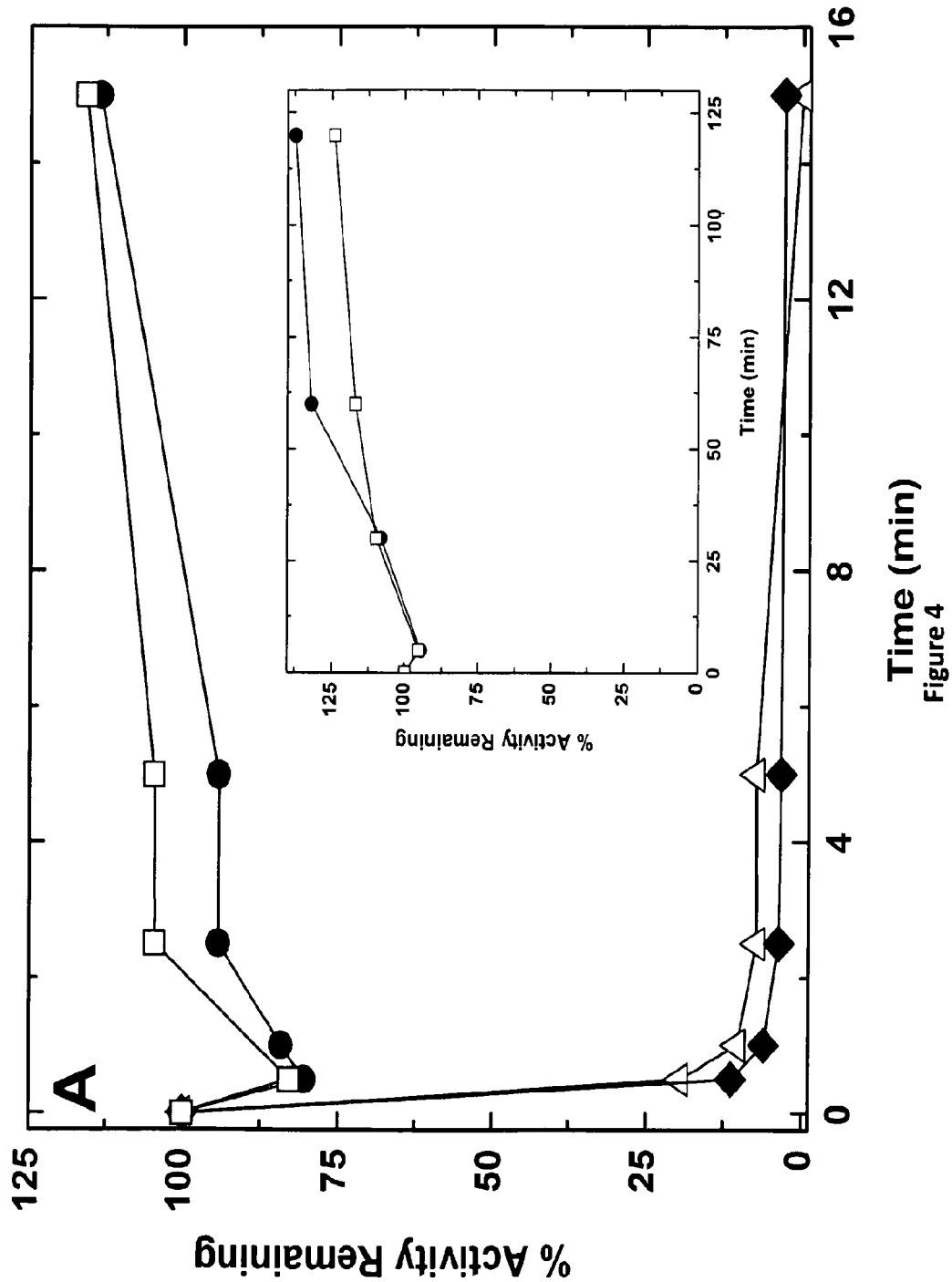
Figure 4:
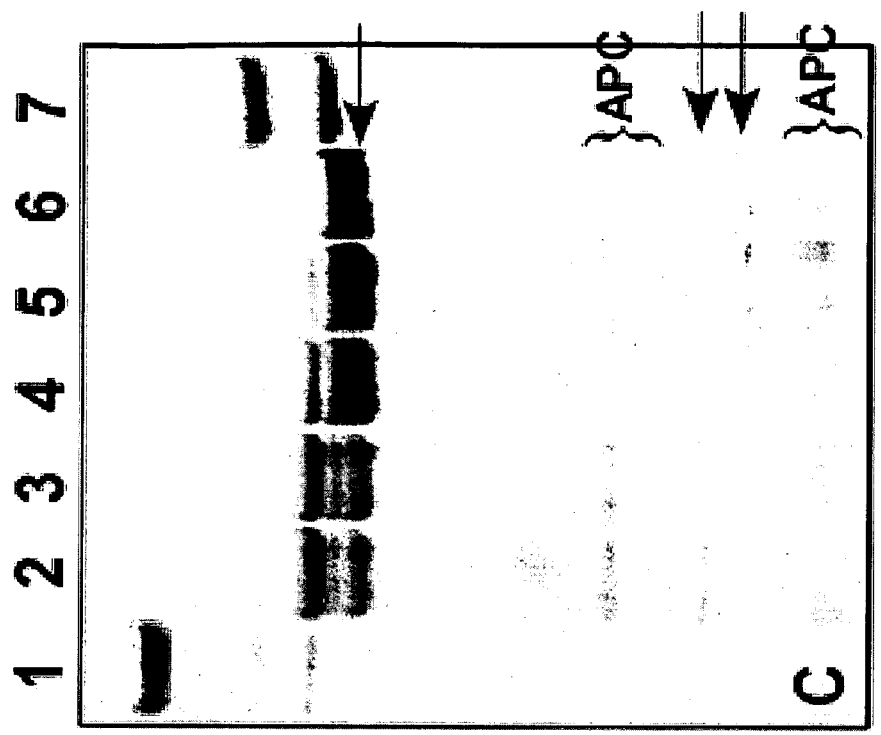
Figure 4:
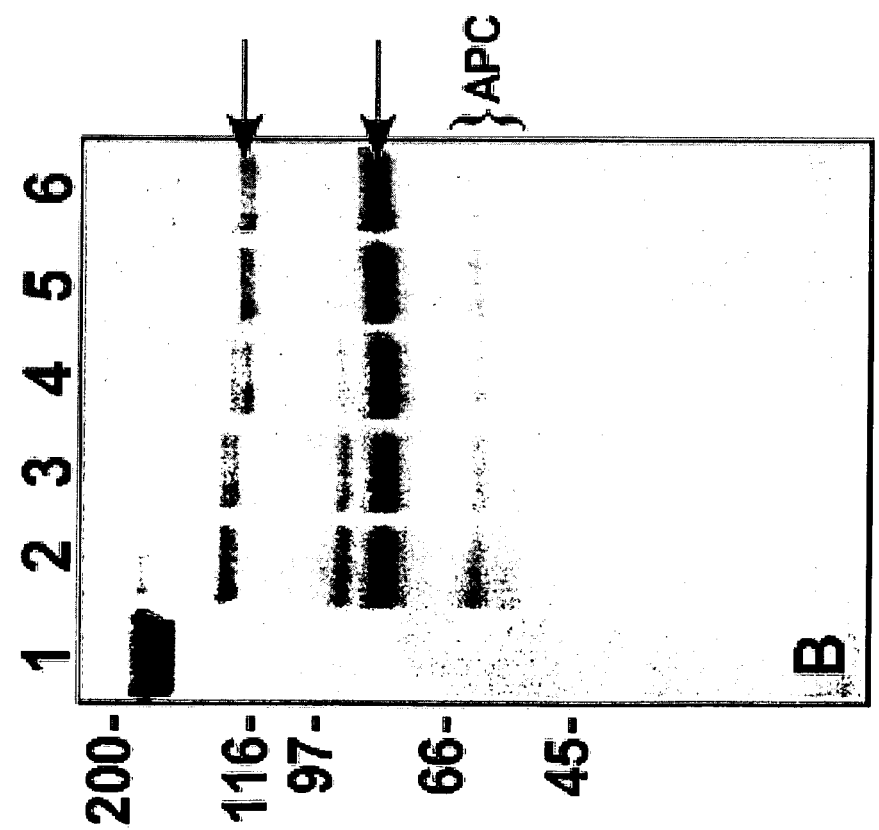

FIG. 4. Inactivation of membrane-bound FV(a) by APC. Reaction mixtures containing 50 μM PCPS and 500 nM pt-rFV (-●-), pt-rFVa (-□-), hFV-810 (-◆-), or rFVa (-△-) were incubated with either 10 nM or 750 nM (inset) APC. At selected time intervals, samples were removed and assayed for cofactor activity as described in "Experimental Procedures" (panel A) or run on a SDS-PAGE gel and stained with Coomassie Blue R250 under reducing (panel B) or non-reducing conditions (panel C). The data are representative of two similar experiments.

FIG. 5. Nucleic Acid Coding sequence for Factor V. The nucleic acid sequence of the snake venom derived Factor V (SEQ ID NO: 1) is shown in panels 5A and 5B. The nucleic acid sequence of the snake venom derived Factor V (SEQ ID NO: 2) which has been codon optimized for expression in mammalian systems is shown in panels 5C and 5D.

DETAILED DESCRIPTION OF THE INVENTION

Venomous snakes produce a diverse array of toxic compounds, including procoagulants to defend themselves and incapacitate prey. The Australian brown snake Pseudonaja textilis has a venom-derived prothrombin activator complex which is homologous to factor Xa (FXa) and factor V (FV). The FV component (pt-FV) has a similar domain organization as human FV however its central B-domain is much smaller (55 versus 836 amino acids). Here, pt-FV has acquired unique gain of function elements transforming it into a potent procoagulant. Measurements using recombinant pt-FV revealed that it is synthesized as a constitutively active cofactor, which unlike human FV, does not require proteolysis to express activity. Sequence comparisons showed that it has lost a conserved cluster of basic amino acids within the B-domain which serve to stabilize the inactive procofactor state. Remarkably, pt-FV also functions in the absence of negatively charged phospholipids as it binds snake FXa with high affinity and exhibits equivalent kinetic parameters for prethrombin-1 in the absence or presence of membranes. Furthermore, pt-FV is functionally resistant to activated protein C even at concentrations resulting in proteolysis of the heavy chain. This stability is likely due in part to a unique disulfide bond linking the heavy and light chains. Together, the confluence of these molecular innovations has transformed pt-FV into a procoagulant biological weapon. These findings provide key new insights into how FV is kept as a procofactor and have broad implications for better understanding how FXa-FVa interactions contributes to the enhanced function of prothrombinase.

Thus, the invention also provides a unique derivative of factor V (FV) which is expressed in the venom of the common brown snake P. textilis or heterologous expression systems (pt-FV) or a human FV derivative expressed in similar systems that has one or more of the following unique characteristics:

a) a FV variant that is synthesized in an active, cofactor state, b) a FV variant that has a unique conformation such as to allow it to bypass the normal requirement for a membrane surface to achieve high affinity binding to its serine protease factor Xa (FXa);

c) a FV variant that is rendered functionally resistant to inactivation by activated protein C (APC), via inclusion of a unique disulfide bond connecting its heavy and light chains.

I. Definitions

Various terms relating to the biological molecules of the present invention are used hereinabove and also throughout the specification and claims.

The phrase "variant FV" refers to a derivative FV molecule obtainable from snake or other heterologous expression systems which exhibits potent procoagulant activity. The variant FV of the invention encoded by SEQ ID NO: 1 or variations thereof (i.e. SEQ ID NO: 2) are compatible for use in humans and promotes desirable FV procoagulant activity.

The phrase "hemostasis related disorder" or "blood coagulation disorder" refers to bleeding disorders such as hemophilia A and B, hemophilia A and B patients with inhibitory antibodies, deficiencies in coagulation Factors, VIII IX and X, XI, V, XII, II, von Willebrand factor, combined FV/FV1 deficiency, vitamin K epoxide reductase C1 deficiency, gamma-carboxylase deficiency; bleeding associated with trauma, injury, thrombosis, thrombocytopenia, stroke, coagulopathy, disseminated intravascular coagulation (DIC); over-anticoagulation associated with heparin, low molecular weight heparin, pentasaccharide, warfarin, small molecule antithrombotics (i.e. FXa inhibitors); and platelet disorders such as, Bernard Soulier syndrome, Glanzman thromblastemia, and storage pool deficiency.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote. With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "promoter region" refers to the transcriptional regulatory regions of a gene, which may be found at the 5' or 3' side of the coding region, or within the coding region, or within introns.

The term "vector" refers to a small carrier DNA molecule into which a DNA sequence can be inserted for introduction into a host cell where it will be replicated. An "expression vector" is a specialized vector that contains a gene or nucleic acid sequence with the necessary regulatory regions needed for expression in a host cell. The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, of the compound of interest. Purity is measured by methods appropriate for the compound of interest (e.g. chromatographic methods, agarose or polyacrylamide gel electrophoresis, HPLC analysis, and the like).

The phrase "consisting essentially of" when referring to a particular nucleotide sequence or amino acid sequence means a sequence having the properties of a given SEQ ID NO:. For example, when used in reference to an amino acid sequence, the phrase includes the sequence per se and molecular modifications that would not affect the basic and novel characteristics of the sequence.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application for which the oligonucleotide is used.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15-25 or more nucleotides, although it may contain fewer nucleotides.

The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically. The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to act functionally as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 31 terminus by the addition of nucleotides by the action of a polymerase or similar activity to yield a primer extension product.

The primer may vary in length depending on the particular conditions and requirements of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "percent identical" is used herein with reference to comparisons among nucleic acid or amino acid sequences. Nucleic acid and amino acid sequences are often compared using computer programs that align sequences of nucleic or amino acids thus defining the differences between the two. For purposes of this invention comparisons of nucleic acid sequences are performed using the GCG Wisconsin Package version 9.1, available from the Genetics Computer Group in Madison, Wis. For convenience, the default parameters (gap creation penalty=12, gap extension penalty=4) specified by that program are intended for use herein to compare sequence identity. Alternately, the Blastn 2.0 program provided by the National Center for Biotechnology Information (on the world wide web at .ncbi.nlm.nih.gov/blast/; Altschul et al., 1990, J MoI Biol 215:403-410) using a gapped alignment with default parameters, may be used to determine the level of identity and similarity between nucleic acid sequences and amino acid sequences.

II. Preparation of Variant Forms of FV Encoding Nucleic Acid Molecules, Polypeptides and Derivatives Thereof Nucleic Acid Molecules Nucleic acid molecules encoding the variant forms of FV or functional derivatives thereof of the invention may be prepared by using recombinant DNA technology methods. The availability of nucleotide sequence information enables preparation of isolated nucleic acid molecules of the invention by a variety of means. For example, nucleic acid sequences encoding the variant forms of FV or derivative thereof polypeptide may be isolated from appropriate biological sources using standard protocols well known in the art.

Nucleic acids of the present invention may be maintained as DNA in any convenient cloning vector. In a preferred embodiment, clones are maintained in a plasmid cloning/expression vector, such as pBluescript (Stratagene, La Jolla, Calif.), which is propagated in a suitable *E. coli* host cell. Alternatively, the nucleic acids may be maintained in vector suitable for expression in mammalian cells. In cases where post-translational modification affects the variant forms of FV or derivative thereof function, it is preferable to express the molecule in mammalian cells. The variant FV or derivative thereof-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting the FV expression.

Proteins

A full-length variant of FV or derivative thereof polypeptide of the present invention may be prepared in a variety of ways, according to known methods. The protein may be purified from appropriate sources, e.g., transformed bacterial or animal cultured cells or tissues which express the activated form of FV, by immunoaffinity purification. However, this is not a preferred method due to the low amount of protein likely to be present in a given cell type at any time. The availability of nucleic acid molecules encoding a variant form of FV or derivative thereof polypeptide enables production of the variant form of FV or derivative thereof using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, Md.

Alternatively, according to a preferred embodiment, larger quantities of the variant form of FV or derivative thereof may be produced by expression in a suitable prokaryotic or eukaryotic expression system. For example, part or all of a DNA molecule encoding the variant form of FV for example, may be inserted into a plasmid vector adapted for expression in a bacterial cell, such as *E. coli* or a mammalian cell such as CHO or HeLa cells. Alternatively, in a preferred embodiment, tagged fusion proteins comprising the variant form of FV or derivative thereof can be generated. Such FV molecules or derivative thereof-tagged fusion proteins are encoded by part or all of a DNA molecule, ligated in the correct codon reading frame to a nucleotide sequence encoding a portion or all of a desired polypeptide tag which is inserted into a plasmid vector adapted for expression in a bacterial cell, such as *E. coli* or a eukaryotic cell, such as, but not limited to, yeast and mammalian cells. Vectors such as those described above comprise the regulatory elements necessary for expression of the DNA in the host cell positioned in such a manner as to permit expression of the DNA in the host cell. Such regulatory elements required for expression include, but are not limited to, promoter sequences, transcription initiation sequences, and enhancer sequences.

The snake venom derived variant FV or derivative thereof protein, produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope, GST or the hemagglutinin epitope. Such methods are commonly used by skilled practitioners.

The FV or derivative thereof proteins, prepared by the aforementioned methods, may be analyzed according to standard procedures. For example, such proteins may be subjected to amino acid sequence analysis, according to known methods.

As discussed above, a convenient way of producing a polypeptide according to the present invention is to express nucleic acid encoding it, by use of the nucleic acid in an expression system. A variety of expression systems of utility for the methods of the present invention are well known to those of skill in the art.

Accordingly, the present invention also encompasses a method of making a polypeptide (as disclosed), the method including expression from nucleic acid encoding the polypeptide (generally nucleic acid). This may conveniently be achieved by culturing a host cell, containing such a vector, under appropriate conditions which cause or allow production of the polypeptide. Polypeptides may also be produced in in vitro systems, such as reticulocyte lysate.

III. Uses of FV Encoding Nucleic Acids and Proteins or Derivatives Thereof

The FV polypeptide or derivative thereof or nucleic acids encoding the same having altered coagulation activities may be used according to this invention, for example, as therapeutic and/or prophylactic agents which modulate the blood coagulation cascade. The present inventors have discovered that these molecules can be altered to increase coagulation.

In a preferred embodiment of the present invention, the FV or derivative thereof may be administered to a patient via infusion in a biologically compatible carrier, preferably via intravenous injection. The FV or derivative thereof of the invention may optionally be encapsulated into liposomes or mixed with other phospholipids or micelles to increase stability of the molecule. The FV or derivative thereof may be administered alone or in combination with other agents known to modulate hemostasis (e.g., Factor VIIa, FIX, FVIII or FX/Xa and derivatives thereof). An appropriate composition in which to deliver FV or derivative thereof may be determined by a medical practitioner upon consideration of a variety of physiological variables, including, but not limited to, the patient's condition and hemodynamic state. A variety of compositions well suited for different applications and routes of administration are well known in the art and are described hereinbelow. The preparation containing the purified FV or derivative thereof contains a physiologically acceptable matrix and is preferably formulated as a pharmaceutical preparation. The preparation can be formulated using substantially known prior art methods, it can be mixed with a buffer containing salts, such as NaCl, $CaCl_2$, and amino acids, such as glycine and/or lysine, and in a pH range from 6 to 8.

Until needed, the purified preparation containing the factor V or derivative thereof can be stored in the form of a finished solution or in lyophilized or deep-frozen form. Preferably the preparation is stored in lyophilized form and is dissolved into a visually clear solution using an appropriate reconstitution solution, Alternatively, the preparation according to the present invention can also be made available as a liquid preparation or as a liquid that is deep-frozen.

The preparation according to the present invention is especially stable, i.e., it can be allowed to stand in dissolved form for a prolonged time prior to application. The preparation according to the present invention can be made available as a pharmaceutical preparation with the FV or derivative thereof in the form of a one-component preparation or in combination with other factors in the form of a multi-component preparation.

Prior to processing the purified protein into a pharmaceutical preparation, the purified protein is subjected to the conventional quality controls and fashioned into a therapeutic form of presentation. In particular, during the recombinant manufacture, the purified preparation is tested for the absence of cellular nucleic acids as well as nucleic acids that are derived from the expression vector, preferably using a method, such as is described in EP 0 714 987.

Another feature of this invention relates to making available a preparation which contains FV or derivative thereof with a high stability and structural integrity and which, in particular, is free from inactive factor V/Va analog intermediates and autoproteolytic degradation products and which can be produced by activating a factor V analog of the type described above and by formulating it into an appropriate preparation. The pharmaceutical preparation may contain dosages of between 10-1000 µg/kg, more preferably between about 10-250 µg/kg and most preferably between 10 and 75 µg/kg, with 40 µg/kg of the variant factor V polypeptide being particularly preferred. Patients may be treated immediately upon presentation at the clinic with a bleed. Alternatively, patients may receive a bolus infusion every one to three hours, or if sufficient improvement is observed, a once daily infusion of FV or derivative thereof described herein.

The FV or derivative thereof-encoding nucleic acids obtained from snake may be used for a variety of purposes in accordance with the present invention. In a preferred embodiment of the invention, a nucleic acid delivery vehicle (i.e., an expression vector) for modulating blood coagulation is provided wherein the expression vector comprises a nucleic acid sequence coding the FV or derivative thereof polypeptide, or a functional fragment thereof as described herein. Administration of FV or derivative thereof-encoding expression vectors to a patient, results in the expression of FV or derivative thereof polypeptide which serves to enhance coagulation. In accordance with the present invention, the FV or derivative thereof encoding nucleic acid sequence may encode FV or derivative thereof polypeptide as described herein whose expression modulates hemostasis.

Expression vectors comprising FV or derivative thereof nucleic acid sequences may be administered alone, or in combination with other molecules useful for modulating hemostasis. According to the present invention, the expression vectors or combination of therapeutic agents may be administered to the patient alone or in a pharmaceutically acceptable or biologically compatible composition.

In a preferred embodiment of the invention, the expression vector comprising nucleic acid sequences encoding FV or derivative thereof is a viral vector. Viral vectors which may be used in the present invention include, but are not limited to, adenoviral vectors (with or without tissue specific promoters/ enhancers), adeno-associated virus (AAV) vectors of multiple serotypes (e.g., AAV-2, AAV-5, AAV-7, and AAV-8) and hybrid AAV vectors, lentivirus vectors and pseudo-typed lentivirus vectors [e.g., Ebola virus, vesicular stomatitis virus (VSV), and feline immunodeficiency virus (FIV)], herpes simplex virus vectors, vaccinia virus vectors, and retroviral vectors.

In a preferred embodiment of the present invention, methods are provided for the administration of a viral vector comprising nucleic acid sequences FV or derivative thereof, or a functional fragment thereof. Adenoviral vectors of utility in the methods of the present invention preferably include at least the essential parts of adenoviral vector DNA. As described herein, expression of FV or derivative thereof polypeptide following administration of such an adenoviral vector serves to modulate hemostasis.

Recombinant adenoviral vectors have found broad utility for a variety of gene therapy applications. Their utility for such applications is due largely to the high efficiency of in vivo gene transfer achieved in a variety of organ contexts.

Adenoviral particles may be used to advantage as vehicles for adequate gene delivery. Such virions possess a number of desirable features for these applications, including: structural features related to being a double stranded DNA nonenveloped virus and biological features such as a tropism for the human respiratory system and gastrointestinal tract. Moreover, adenoviruses are known to infect a wide variety of cell types in vivo and in vitro by receptor-mediated endocytosis. Attesting to the overall safety of adenoviral vectors, infection with adenovirus leads to a minimal disease state in humans which comprises mild flu-like symptoms.

Due to their large size (~36 kilobases), adenoviral genomes are well suited for use as gene therapy vehicles because they can accommodate the insertion of foreign DNA following the removal of adenoviral genes essential for replication and nonessential regions. Such substitutions render the viral vector impaired with regard to replicative functions and infectivity. Of note, adenoviruses have been used as vectors for gene therapy and for expression of heterologous genes.

For a more detailed discussion of the use of adenovirus vectors utilized for gene therapy, see Berkner, 1988, Biotechniques 6:616-629 and Trapnell, 1993, Advanced Drug Delivery Reviews 12: 185-199.

It is desirable to introduce a vector that can provide, for example, multiple copies of a desired gene and hence greater amounts of the product of that gene. Improved adenoviral vectors and methods for producing these vectors have been described in detail in a number of references, patents, and patent applications, including: Mitani and Kubo (2002, Curr Gene Ther. 2(2): 135-44); Olmsted-Davis et al. (2002, Hum Gene Ther. 13(11): 1337-47); Reynolds et al. (2001, Nat Biotechnol. 19(9): 838-42); U.S. Pat. No. 5,998,205 (wherein tumor-specific replicating vectors comprising multiple DNA copies are provided); U.S. Pat. No. 6,228,646 (wherein helper-free, totally defective adenovirus vectors are described); U.S. Pat. No. 6,093,699 (wherein vectors and methods for gene therapy are provided); U.S. Pat. No. 6,100, 242 (wherein a transgene-inserted replication defective adenovirus vector was used effectively in in vivo gene therapy of peripheral vascular disease and heart disease); and International Patent Application Nos. WO 94/17810 and WO 94/23744.

For some applications, an expression construct may further comprise regulatory elements which serve to drive expression in a particular cell or tissue type. Such regulatory elements are known to those of skill in the art and discussed in depth in Sambrook et al. (1989) and Ausubel et al. (1992). The incorporation of tissue specific regulatory elements in the expression constructs of the present invention provides for at least partial tissue tropism for the expression of FV or derivative thereof or functional fragments thereof. For example, an E1 deleted type 5 adenoviral vector comprising nucleic acid sequences encoding FV or derivative thereof under the control of a cytomegalovirus (CMV) promoter may be used to advantage in the methods of the present invention.

Exemplary Methods for Producing Adenoviral Vectors

Adenoviral vectors for recombinant gene expression have been produced in the human embryonic kidney cell line 293 (Graham et al., 1977, J, Gen. Virol. 36:59-72). This cell line is permissive for growth of adenovirus 2 (Ad2) and adenovirus 5 mutants defective in E1 functions because it comprises the left end of the adenovirus 5 genome and, therefore, expresses E1 proteins. E1 genes integrated into the cellular genome of 293 cells are expressed at levels which facilitate the use of these cells as an expression system in which to amplify viral vectors from which these genes have been deleted. 293 cells have been used extensively for the isolation and propagation of E1 mutants, for helper-independent cloning, and for expression of adenovirus vectors. Expression systems such as the 293 cell line, therefore, provide essential viral functions in trans and thereby enable propagation of viral vectors in which exogenous nucleic acid sequences have been substituted for E1 genes. See Young et al. in The Adenoviruses, Ginsberg, ed., Plenum Press, New York and London (1984), pp. 125-172.

Other expression systems well suited to the propagation of adenoviral vectors are known to those of skill in the art (e.g., HeLa cells) and have been reviewed elsewhere. Also included in the present invention is a method for modulating hemostasis comprising providing cells of an individual with a nucleic acid delivery vehicle encoding FV or derivative thereof polypeptide and allowing the cells to grow under conditions wherein the FV or derivative thereof polypeptide is expressed.

From the foregoing discussion, it can be seen that variant FV or derivative thereof polypeptide or nucleic acids encoding the same may be used in the treatment of disorders associated with aberrant blood coagulation.

Pharmaceutical Compositions

The expression vectors of the present invention may be incorporated into pharmaceutical compositions that may be delivered to a subject, so as to allow production of a biologically active protein (e.g., fFV or derivative thereof polypeptide or functional fragment or derivative thereof). In a particular embodiment of the present invention, pharmaceutical compositions comprising sufficient genetic material to enable a recipient to produce a therapeutically effective amount of FV or derivative thereof polypeptide can influence hemostasis in the subject. Alternatively, as discussed above, an effective amount of the variant Factor V polypeptide may be directly infused into a patient in need thereof. The compositions may be administered alone or in combination with at least one other agent, such as a stabilizing compound, which may be administered in any sterile, biocompatible pharmaceutical carrier, including, but not limited to, saline, buffered saline, dextrose, and water. The compositions may be administered to a patient alone, or in combination with other agents which influence hemostasis. In preferred embodiments, the pharmaceutical compositions also contain a pharmaceutically acceptable excipient. Such excipients include any pharmaceutical agent that does not itself induce an immune response harmful to the individual receiving the composition, and which may be administered without undue toxicity. Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., 18th Edition, Easton, Pa. [1990]).

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions. For topical or nasal administration, penetrants appropriate to the particular barrier to be permeated are used in the formulation. Such penetrants are generally known in the art. The pharmaceutical compositions of the present invention may be manufactured in any manner known in the art (e.g., by means of conventional mixing, dissolving, granulating, dragee-making, levigating, emulsifying, encapsulating, entrapping, or lyophilizing processes).

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding, free base forms. In other cases, the preferred preparation may be a lyophilized powder which may contain any or all of the following: 1-50 μM histidine, 1%-2% sucrose, and 2-7% mannitol, at a pH range of 4.5 to 5.5, which is combined with buffer prior to use.

After pharmaceutical compositions have been prepared, they may be placed in an appropriate container and labeled for treatment. For administration of FV or derivative thereof-containing vectors, such labeling would include amount, frequency, and method of administration.

Pharmaceutical compositions suitable for use in the invention include compositions wherein the active ingredients are contained in an effective amount to achieve the intended therapeutic purpose. Determining a therapeutically effective dose is well within the capability of a skilled medical practitioner using the techniques provided in the present invention. Therapeutic doses will depend on, among other factors, the age and general condition of the subject, the severity of the aberrant blood coagulation phenotype, and the strength of the control sequences regulating the expression levels of FV or derivative thereof polypeptide. Thus, a therapeutically effective amount in humans will fall in a relatively broad range that may be determined by a medical practitioner based on the response of an individual patient to vector-based form of or protein infused FV or derivative thereof treatment.

Administration

The variant activated form of FV polypeptide, alone or in combination with other agents may be directly infused into a patient in an appropriate biological carrier as described hereinabove. Expression vectors of the present invention comprising nucleic acid sequences encoding the activated form of FV or derivative thereof, or functional fragments thereof, may be administered to a patient by a variety of means (see below) to achieve and maintain a prophylactically and/or therapeutically effective level of the activated form of FV or derivative thereof polypeptide. One of skill in the art could readily determine specific protocols for using the activated form of FV or derivative thereof encoding expression vectors of the present invention for the therapeutic treatment of a particular patient. Protocols for the generation of adenoviral vectors and administration to patients have been described in U.S. Pat. Nos. 5,998,205; 6,228,646; 6,093,699; 6,100,242; and International Patent Application Nos. WO 94/17810 and WO 94/23744., which are incorporated herein by reference in their entirety. The activated form of FV or derivative thereof encoding adenoviral vectors of the present invention may be administered to a patient by any means known. Direct delivery of the pharmaceutical compositions in vivo may generally be accomplished via injection using a conventional syringe, although other delivery methods such as convection-enhanced delivery are envisioned (See e.g., U.S. Pat. No. 5,720,720). In this regard, the compositions may be delivered subcutaneously, epidermally, intradermally, intrathecally, intraorbitally, intramucosally, intraperitoneally, intravenously, intraarterially, orally, intrahepatically or intramuscularly. Other modes of administration include oral and pulmonary administration, suppositories, and transdermal applications. A clinician specializing in the treatment of patients with blood coagulation disorders may determine the optimal route for administration of the adenoviral vectors comprising the activated form of FV or derivative thereof nucleic acid sequences based on a number of criteria, including, but not limited to: the condition of the patient and the purpose of the treatment (e.g., enhanced blood coagulation).

Alternatively, the compositions of the invention may be used to induce coagulation topically for wounds and traumatic injury. In this approach, the Factor V of the invention will be formulated for topical application and used on the battlefield or under circumstances in the field where bleeding must stopped or significantly stanched.

The present invention also encompasses AAV vectors comprising a nucleic acid sequence encoding the activated form of FV or derivative thereof polypeptide.

Also provided are lentivirus or pseudo-typed lentivirus vectors comprising a nucleic acid sequence encoding an activated form of FV or derivative thereof polypeptide Also encompassed are naked plasmid or expression vectors comprising a nucleic acid sequence encoding an activated form of FV or derivative thereof polypeptide.

The following materials and methods are provided to facilitate practice of the Example set forth below.

Reagents

The inhibitors benzamidine and 4-amidinophenyl-methanesulfonyl fluoride hydrochloride (APMSF) were from Sigma (St. Louis, MO) and dansylarginine-N-(3-ethyl-1,5-pentanediyl)amide (DAPA) was from Haematologic Technologies (Essex Junction, Vt.). The peptidyl substrate H-D-phenylalanyl-L-pipecolyl-L-arginyl-p-nitroanilide (S2238) was from Diapharma (West Chester, Ohio). All tissue culture reagents were from Invitrogen (Carlsbad, Calif.), except insulin-transferrin-sodium selenite (ITS; Roche Applied Science, Indianapolis, Ind.). Small unilamellar phospholipids vesicles (PCPS) composed of 75% (w/w) hen egg L-α-phosphatidylcholine and 25% (w/w) porcine brain L-α-phosphatidylserine (Avanti Polar lipids, Alabaster, Ala.) were prepared and characterized as described (22).

Proteins

Human prothrombin was isolated from plasma as described previously (23). Prethrombin-1 and prethrombin-2 were purified by established procedures (18), and thrombin was obtained from Haematologic Technologies. A constitutively active partial B-domainless form of FV (hFV-810), rFVa, rFX and rFXa were prepared, purified and characterized as described (3, 24, 25). The purified enzymatic subunit of pseutarin C (pt-FXa) was a generous gift from QRxPharma (Sydney, Australia). Recombinant hirudin was obtained from EMD-Chemicals (San Diego, Calif.). Recombinant tick anticoagulant protein and human APC were obtained from Dr. Sriram Krishnaswamy (The Children's Hospital of Philadelphia). Molecular weights and extinction coefficients ($E_{0.1\%, 280\ nm}$) of the various proteins used were: prothrombin, 72,000 and 1.47 (18); prethrombin-1 49,900 and 1.78 (18); prethrombin-2, 37,500 and 1.95 (18); thrombin, 37,500 and 1.94 (26); rFXa 46,000 and 1.16 (27); rFVa, 175,000 and 1.78 (3); rFV-810: 216,000, 1.54 (3), and pt-FV: 170,000, 1.50 (present study). For pt-FXa, values for the human protein were used. Unless otherwise noted, all functional assays were performed at 25° C. in 20 mM Hepes, 0.15 M NaCl, 2 mM $CaCl_2$, 0.1% polyethylene glycol 8000, pH 7.5 (assay buffer).

Analytical Ultracentrifugation

Molecular weights were determined in a Beckman Optima XL-I analytical ultracentrifuge using interference optics. Sedimentation velocity was measured at 20° C. in 20 mM Hepes, 150 mM NaCl, 5 mM $CaCl_2$, pH 7.4 at 25,000 rpm with an AN60Ti rotor. Protein concentrations were: pt-rFV, 0.60 mg/mL (3.6 µM) and pt-FXa, 0.18 mg/mL (3.9 µM). Sedimentation coefficients and molecular weights were determined by g(s*) analysis (28). Extinction coefficients were determined by differential refractometry by the procedure described by Babul and Stellwagen (29).

Construction of rFV Variants

The *P. textilis* FV cDNA derived from the venom gland (8) was modified with flanking XmaI restriction sites and then subcloned into the pED expression plasmid (3). The cDNA was further modified by exchanging sequences encoding the signal sequence of *P. textilis* FV with that of human FV using the technique of splicing by overlap extension (30). The final construct, pED-FV-ptex, encoded for the human FV signal peptide (residues −28 to −1) followed by the mature venom-derived pt-FV protein (residues 1-1430). Sequence analysis indicated that the *P. textilis* FV cDNA displayed the same sequence as reported by Rao et al. (7), except for codons 50 (Lys) and 1305 (Phe), which are identical to the homologous residues of *O. scutellatus* and *O. microlepidotus* (8). A pt-FV variant with $Arg^{742}$ and $Arg^{788}$ replaced by Gln (pt-FV-QQ) was generated with the QuickChange site-directed mutagenesis kit (Stratagene, La Jolla, Calif.) using appropriate mutagenic complementary oligonucleotides. These amino acids are homologous to $Arg^{709}$ and $Arg^{1545}$ in human FV and represent thrombin cleavage sites. Following mutagenesis, the entire cDNA was sequenced in order to confirm the presence of the desired mutations and to ensure that there were no polymerase-induced errors.

Expression and Purification of pt-rFV

Plasmids encoding pt-FV or pt-FV-QQ were introduced into baby hamster kidney (BHK) cells and high producing stable clones were established as described (3). Cells were expanded into triple flasks and cultured in DMEM/F12 media supplemented with ITS and 2.5 mM $CaCl_2$. Conditioned media was collected for 4-6 days, centrifuged, and stored at −20° C. in the presence of 10 μM APMSF and 1 mM Benzamidine. For purification, media was thawed at 37° C. and loaded onto a 30 mL Q-Sepharose FF column (Amersham Biosciences, Piscataway, N.J.) equilibrated in 20 mM Hepes, 0.15 M NaCl, 5 mM $CaCl_2$, pH 7.4. The column was washed with the same buffer and eluted with a 0.15-1 M NaCl gradient. Fractions were collected and analyzed by SDS-PAGE and by a FV-specific clotting assay as described (3). Fractions containing pt-rFV were pooled and dialyzed versus 20 mM MES, 2 mM $CaCl_2$, pH 6.0. and then loaded on a Poros HS/20 column (10×100 mm; Applied Biosystems, Foster City, Calif.) equilibrated with the same buffer. The column was washed with 20 mM MES, 2 mM $CaCl_2$, pH 6.0 and then eluted with a 0-0.6 M NaCl gradient. FV containing fractions were pooled and dialyzed versus 20 mM Hepes, 0.15 M NaCl, 2 mM $CaCl_2$, pH 7.4, and the protein was stored at −80° C. The final yield was ~4 mg of pt-rFV/liter of conditioned media.

Protein Characterization

Protein purity was assessed by SDS-PAGE using pre-cast 4-12% gradient gels (Invitrogen) under non-reducing and reducing conditions (50 mM dithiothreitol) employing the MOPS buffer system followed by staining with Coomassie Brilliant Blue R-250. N-terminal sequence analysis was performed in the laboratory of Dr. Alex Kurosky and Steve Smith at the University of Texas Medical Branch at Galveston or Dr. Jan Pohl, Center for Disease Control (Atlanta, Ga.). Chemical γ-carboxyglutamic acid (Gla) analysis on pt-FXa was carried out in the laboratory as described (24).

Kinetics of Protein Substrate Cleavage

Steady state initial velocities of macromolecular substrate cleavage were determined discontinuously at 25° C. as described (25). The kinetic parameters of prothrombinase or FXa-FVa-catalyzed prothrombin or prethrombin-1 activation ($K_m$ and $V_{max}$) were determined in assay buffer by measuring the initial rate of thrombin formation at increasing concentrations of macromolecular substrate. Assay mixtures contained PCPS (50 μM), DAPA (3 μM), the various pt-rFV(a) cofactor species (20 nM), and various concentrations of prothrombin (0-5.0 μM) or prethrombin-1 (0-15 μM). The reaction was initiated with pt-FXa (0.1 nM). When prethrombin-2 was used as protein substrate, the following reaction conditions were used: PCPS (50 μM), DAPA (3 μM), and prethrombin-2 (1.4 μM) were incubated with the various FV(a) cofactors (0-40 nM), and the reaction was initiated with pt-FXa (5 nM). For certain experiments, PCPS was omitted from the reaction mixture (see figure legends). For experiments in which pt-rFVa was used, pt-rFV (600 nM) was incubated with 2 nM thrombin at 37° C. for 15 min followed by the addition of 2.4 nM hirudin.

APC Inactivation of pt-rFV

The inactivation of the various cofactor proteins (500 nM; pt-rFV, pt-rFVa, rhFVa, or h-FV-810) in the presence of PCPS (50 μM) was initiated by APC addition (10 nM or 750 nM). Aliquots of the reaction mixture were withdrawn at the indicated time intervals and assessed by SDS-PAGE (4-12% gel) and through assessment of functional activity. In this assay, residual cofactor activity was assessed by measuring the effect of FVa on prothrombin activation essentially as described (25). Assay mixtures contained, 1.4 μM prothrombin, 50 μM PCPS, 3 μM DAPA, 1 nM FV(a), and 1 nM pt-FXa. With rhFVa or hFV-810, human rFXa was used instead. Under these conditions, the initial rate of the reaction was proportional to the concentration of the cofactor.

Data Analysis

Data were analyzed according to the referenced equations by nonlinear least squares regression analysis using the Marquardt algorithm (31). The qualities of the fits were assessed by the criteria described (32). Reported estimates of error represent ±2 S.D. The dissociation constant ($K_d$) for the interaction between pt-FXa and pt-rFV(a) were obtained from the dependence of the initial rate of prethrombin-2 activation on the concentrations of the cofactor species with the stoichiometry fixed at 1 (33). Initial velocity measurements of prothrombin or prethrombin-1 cleavage by prothrombinase were analyzed by fitting the data to the Henri-Michaelis-Menten equation (34), to yield fitted values for $K_m$ and $V_{max}$.

The Examples set forth below are provided to illustrate certain embodiments of the invention. They are not intended to limit the invention in any way.

EXAMPLE I

Snake Venom Derived or Human Derivative of Factor V for Use in Human Therapy

The present invention describes the biological properties of snake venom derived FV from *P. textilis*. These unique properties, listed below, could also be engineered into a human FV derivative recapitulating the procoagulant properties. These properties are: a) pt-FV exists in an active, cofactor state and is as such the first example of a naturally occurring active FV variant; b) pt-FV has a unique conformation as it bypasses the normal requirement for a membrane surface to achieve high affinity binding to its serine protease factor Xa (FXa); c) pt-FV is functionally resistant to inactivation by activated protein C (APC), due to a unique disulfide bond in pt-FV that connects its heavy and light chains. Engineering a human FV derivative comprising one or more of these characteristics will enhance its procoagulant properties, thereby providing a useful therapeutic tool for treatment of bleeding disorders.

In the present study, a series of functional measurements with recombinant venom-derived FV (pt-rFV) from *P. textilis* as well as highly purified venom-derived FXa (pt-FXa) have been used to investigate the biological properties of this unique form of FV and examine the mechanistic basis for the strong procoagulant nature of the venom-derived prothrombinase complex. This work demonstrates that pt-rFV has adapted into a potent procoagulant by acquiring multiple gain of function elements not known to occur in mammalian FV. The findings shed new light on multiple aspects of FV structure/function relationships, facilitate bioengineering FV for therapeutic purposes, and also highlight the remarkable ability of nature to enhance the existing properties of a protein for selective advantage.

Results

Expression and Physical Characterization of pt-rFV

Figure 1:
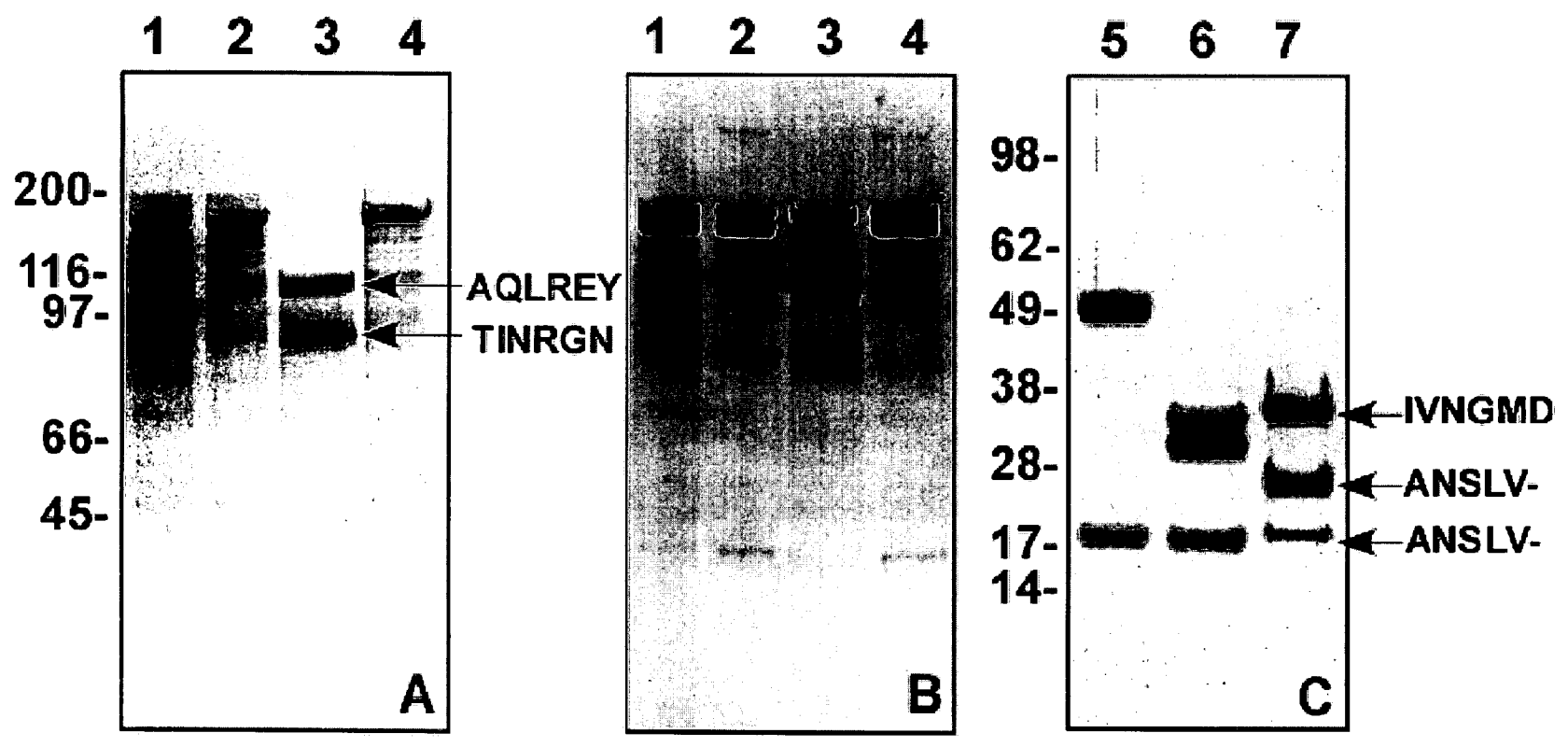

Because of the high protease content of crude snake venom, isolation of a homogenous, uncleaved preparation of pt-FV has not been obtained (12-15). To circumvent this, purified pt-rFV from BHK cells was expressed in high yields. Wild-type pt-rFV and a variant lacking thrombin cleavage sites flanking the heavy and light chains (pt-rFV-QQ) migrated primarily as single bands (~180 kDa) on reducing SDS-PAGE (FIG. 1, panel A). Sedimentation velocity studies indicated that pt-rFV was homogeneous with a molecular weight estimate of 170,000 (Table 1). While pt-rFV-QQ was not cleaved by thrombin, pt-rFV was processed to pt-rFVa, yielding the characteristic heavy and light chains. N-terminal sequence analysis revealed correct processing at the predicted thrombin cleavage sites (FIG. 1) (7, 8). Surprisingly, following thrombin treatment, a large fraction (>60%) of pt-rFVa migrated as a single band under non-reducing conditions (FIG. 1, panel B), indicating that the heavy and light chains are held together by a unique disulfide bond. This likely accounts for migration of pt-rFV and pt-rFV-QQ as doublets under non-reducing conditions. Sequence alignment suggest that pt-FV likely has two free Cys residues in the heavy chain (A2 domain, 539 and 641) and one free Cys in the light chain (A3 domain, 1032) (7).

TABLE 1

Sedimentation velocity studies: hydrodynamic parameters.

| Cofactor species | $s_{20,w} \pm$ S.E. $\times 10^{-13}$ s | $M_r \pm$ S.E. $\times 10^3$ | $E_{280\,nm}$ mg·ml$^{-1}$·cm$^{-1}$ | Ref. |
|---|---|---|---|---|
| rhFVa | 8.03 ± 0.01 | 175 ± 2 | 1.78 | (3) |
| hFV-810 | 8.43 ± 0.04 | 216 ± 4 | 1.54 | (3) |
| pt-rFV | 8.30 ± 0.01 | 170 ± 0.7 | 1.25 | Present |
| pt-rFV + pt-FXa | 9.33 ± 0.01 | 213 ± 2 | N.D.$^a$ | Present |

$^a$N.D., Not determined

FV purified from the crude venom of *P. textilis* or *O. scutellatus* has low activity in the presence of bovine FXa (14, 15). The initial attempts to characterize pt-rFV were consistent with these observations. However, estimates demonstrate that pt-rFV or pt-rFVa have $\approx 1/40^{th}$ the activity compared to human FVa. The low activity appeared to be principally due to the finding that pt-rFV or pt-rFVa bound with a reduced affinity to membrane-bound human FXa ($K_d$>400 nM) using established fluorescent binding measurements (data not shown) (3). Thus to characterize pt-rFV, pt-FXa was used in all subsequent experiments. SDS-PAGE analysis of pt-FXa is presented in FIG. 1 along with N-terminal sequence analysis which gave the expected results. The appearance of the light chain as a doublet is likely due to heterogeneous O-glycosylation (8, 16). Furthermore, chemical Gla analysis of pt-FXa yielded 10.9±0.34 mol Gla/mol protein out of 11 mol Gla/mol protein predicted from sequence alignments (8, 16).

Pt-rFV is a Constitutively Active Cofactor

Because of the unusual nature of the pt-FV B-domain, a series of functional measurements were used to determine whether this domain in venom-derived FV functions to maintain the protein as a procofactor. One concern with functional measurements is feedback proteolysis of pt-rFV by in situ generated thrombin. To accommodate this, reactant concentrations were chosen to minimize proteolysis and a reversible inhibitor of thrombin (DAPA) was included in the assay. Furthermore, pt-rFV-QQ, a variant that is resistant to thrombin-mediated proteolysis (FIG. 1), was prepared. In contrast to human FV (1), assembly of pt-rFV with membrane-bound pt-FXa resulted in the rapid activation of prothrombin (FIG. 2A). Steady state kinetic constants for prothrombin conversion were remarkably similar to those observed for human prothrombinase (Table 2) (3, 17). Interestingly, a B-domain truncated derivative of human FV, hFV-810 (3) was also able to assemble with pt-FXa-membranes and activate prothrombin with comparable kinetic parameters (Table 2). Removal of the short B-domain by thrombin generating pt-rFVa or using the uncleavable variant, pt-rFV-QQ, gave comparable kinetic constants (FIG. 2A and Table 2). These data indicate that, unlike human FV, pt-FV is a constitutively active cofactor and does not require proteolytic removal of the B domain to express procoagulant activity; this represents the first example in nature of a constitutively active form of FV.

TABLE 2

Kinetic constants for macromolecular substrate cleavage.

| | Enzyme/Substrate | | | | | | | |
|---|---|---|---|---|---|---|---|---|
| | Prothrombinase/Prothrombin | | FXa-FVa/Prothrombin | | Prothrombinase/Prethrombin-1 | | FXa-FVa/Prethrombin-1 | |
| | $K_m^a$ μM | $k_{cat}$ min$^{-1}$ | $K_m$ μM | $k_{cat}$ min$^{-1}$ | $K_m$ μM | $k_{cat}$ min$^{-1}$ | $K_m$ μM | $k_{cat}$ min$^{-1}$ |
| pt-rFV | 0.39 ± 0.04 | 1250 ± 38 | 1.83 ± 0.12 | 352 ± 11 | 1.12 ± 0.08 | 1609 ± 28 | 1.09 ± 0.11 | 1569 ± 38 |
| pt-rFVa-QQ | 0.44 ± 0.05 | 1270 ± 39 | 1.87 ± 0.05 | 334 ± 4.0 | 1.17 ± 0.06 | 1672 ± 24 | 1.20 ± 0.11 | 1562 ± 34 |
| pt-rFVa | 0.41 ± 0.03 | 1350 ± 31 | 1.74 ± 0.15 | 347 ± 1.0 | 1.38 ± 0.06 | 2209 ± 26 | 1.38 ± 0.06 | 2174 ± 43 |
| hFV-810 | 0.48 ± 0.07 | 1404 ± 62 | N.A.$^b$ | N.A. | N.D.$^c$ | N.D. | N.D. | N.D. |

$^a$ The errors in the fitted constants represent ± 2 S.D.;

$^b$ NA., Not able to determine a value;

$^b$ N.D., Not determined;

The data are representative of two independent measurements.

Pt-rFV Functions in the Absence of Anionic Membranes

A central view of blood coagulation is that membrane binding of coagulation proteins to cellular surfaces (via phosphatidylserine exposure) is critical for normal hemostasis (2). An unusual observation made with oscutarin and pseutarin C is that venom-derived FXa and FV co-purify as a complex and exhibit some level of activity in the absence of anionic membranes; however, the activity of oscutarin is reported to be substantially increased (>400-fold) in the presence of membranes (12-15). To explore this further, the activity of solution phase pt-FXa-pt-rFV using prothrombin was assessed. Initial rates of prothrombin activation using pt-FXa with pt-rFV, pt-rFV-QQ, or pt-rFVa in the absence of membranes were ~7-8-fold lower compared to rates obtained in the presence of membranes at the same enzyme concentration (FIG. 2B). The reduction in activity was reflected by an increase in the $K_m$ (~4-fold) for prothrombin and a (~4-fold) reduction in the $k_{cat}$. In contrast, in the absence of membranes, hFV-810 had very low activity (>150-fold) compared to the membrane bound cofactor (FIG. 2B).

A difficulty in interpreting these data is that the substrate, prothrombin, binds membranes contributing to enhancing rates of thrombin generation. Furthermore, depending on the solution phase dissociation constant for pt-FXa-pt-rFV, pt-FXa may not have been saturated with pt-rFV, reducing the actual enzyme complex concentration, leading to a decreased rate of prothrombin activation. To address the first point, the rate of prethrombin-1 activation in the presence and absence of membranes was measured. Prethrombin-1 is a derivative of prothrombin lacking the membrane binding Gla and kringle-1 domains (18). Consistent with results using prothrombin, the kinetics of prethrombin-1 activation with membrane-bound pt-FXa using pt-rFV, pt-rFV-QQ, or pt-rFVa were equivalent (FIG. 3A and Table 2) and comparable to kinetic parameters using human prothrombinase (17). Surprisingly however, removal of membranes from the reaction mixture had no appreciable effect on the rate of prethrombin-1 activation as the kinetic parameters for solution phase or membrane-bound pt-FXa-pt-rFV were equivalent (FIG. 3B and Table 2). These data suggest that the decreased rate of prothrombin activation (~7-8 fold) with pt-FXa-pt-rFV was not due to decreased enzyme function but rather to elimination of substrate membrane binding.

Pt-FXa and pt-rFV Form a High Affinity Complex

Since rates of prethrombin-1 activation in the presence or absence of membranes were equivalent, the data suggest that pt-FXa was fully saturated with pt-rFV. To assess this directly however, a functional binding measurement to infer the equilibrium dissociation constant for either membrane-bound or solution phase pt-FXa-pt-rFV was used. Increasing concentrations of cofactor (pt-rFV, pt-rFV-QQ, pt-rFVa, or hFV-810) were incubated with a single, fixed concentration of pt-FXa in the presence or absence of PCPS. Initial rates of prethrombin-2 activation were measured and the data were analyzed to extract the inferred equilibrium dissociation constants for cofactor binding to pt-FXa (Table 3). In the presence of PCPS, the dissociation constant for cofactor binding to pt-FXa was ≈3 nM regardless of the cofactor species. This value is similar to the dissociation constant obtained using membrane-bound human FXa and FVa (3). Surprisingly, the dissociation constant for pt-rFV, pt-FV-QQ, or pt-rFVa increased only 2-3-fold in the absence of membranes ($K_d$≈8 nM). This is in marked contrast to the bovine system in which the solution phase dissociation constant for FXa-FVa is ≈0.8-3.0 μM (19, 20). Sedimentation velocity experiments showed that solution phase pt-rFV-pt-FXa formed a 1:1 stoichiometric complex with a molecular weight of 213,000 and a sedimentation coefficient ($s_{20,w}$) of 9.33. These values are in excellent agreement with results obtained with bovine FXa-FVa (19). In contrast to the venom-derived cofactors, a binding constant for solution phase hFV-810-pt-FXa (Table 3) was not able to be established, suggesting that pt-FXa binding involves unique features on pt-rFV that are not present on hFV-810, at least in solution. Together these data indicate that the pt-FXa-pt-FV complex has bypassed the normal requirement for negatively charged membranes to form a high affinity 1:1 complex that can rapidly activate prothrombin.

TABLE 3

Equilibrium binding constants for prothrombinase and FXa-FVa assembly.

| Cofactor species | $K_d{}^a$ nM + PCPS | $K_d$ nM − PCPS |
|---|---|---|
| pt-rFV | 3.06 ± 0.45 | 8.08 ± 1.23 |
| pt-rFV-QQ | 2.88 ± 0.37 | 9.39 ± 1.51 |
| pt-rFVa | 3.84 ± 0.78 | 7.54 ± 0.62 |
| hFV-810 | 3.76 ± 0.87 | N.A.$^b$ |

$^a$The errors in the fitted constants represent ±2 S.D.;
$^b$N.A., Not able to determine a value;
The data are representative of two independent measurements.

Pt-rFV is Functionally Resistant to APC

APC is an important anticoagulant in the hemostatic system and functions by inactivating both FVa and FVIIIa via limited proteolysis (21). For human FVa, cleavage at Arg$^{306}$, Arg$^{506}$, and Arg$^{679}$ results in A2 domain dissociation, loss of FXa binding and ultimately cofactor function (1). Sequence analysis of pt-FV indicates that these sites are not well conserved suggesting it could be resistant to APC (7). Studies with pseutarin C support this contention (7); however, FXa can protect FVa from inactivation by APC complicating data interpretation (1). To directly investigate whether pt-rFV is resistant to APC, these proteins were incubated in the presence of PCPS and at various time intervals monitored proteolysis by SDS-PAGE and cofactor activity using a purified prothrombin activation assay. Using an APC concentration (10 nM) and reaction times (≤15 min) that resulted in the complete loss of rhFVa or hFV-810 function, pt-rFV or pt-rFVa retained full activity (FIG. 4A) and SDS-PAGE analysis showed only limited cleavage of these proteins (data not shown). However, incubation of pt-rFV with higher concentrations of APC (750 nM) for an extended time period resulted in complete proteolysis pt-rFV (FIG. 4B, C). Analysis of both the reducing and non-reducing gels along with N-terminal sequence analysis indicates that APC cleaves pt-rFV in the A2 domain. Surprisingly, despite complete proteolysis of pt-rFV, the cofactor retained full procoagulant activity (FIG. 4A, inset). The nucleic acid sequence encoding the Factor V variant is provided in FIG. 5.

Discussion

Most blood coagulation proteins are synthesized as inactive precursors, and following proteolytic activation, these proteins assemble on cellular surfaces localized at the site of vessel injury (2). In the present study, pt-FV has circumvented these paradigms as it is synthesized as a constitutively active cofactor and bypasses the need for a membrane surface to assemble with FXa and activate prothrombin. Furthermore, pt-FV is functionally resistant to APC, retaining activity even after proteolytic cleavage. A unique disulfide bond linking the heavy and light chains along with enhanced non-covalent interactions, likely contributes to this functional stability. The confluence of these adaptations has transformed pt-FV into a potent procoagulant and likely provides this snake species with a selective advantage by inducing massive disseminated coagulation following envenomation.

References

1. Mann K G, Kalafatis M (2002) Factor V: A combination of Dr. Jekyll and Mr. Hyde. *Blood* 101:20-30.
2. Mann K G, et al. (1990) Surface dependent reactions of the vitamin K-dependent enzyme complexes. *Blood* 76:1-16.
3. Toso R, Camire R M (2004) Removal of B-domain sequences from factor V rather than specific proteolysis underlies the mechanism by which cofactor function is realized. *J Biol Chem* 279:21643-21650.
4. Zhu H, Toso R, Camire R M (2007) Inhibitory sequences within the B-domain stabilize circulating factor V in an inactive state. *J Biol Chem* 282:15033-15039.
5. Jiang Y, Doolittle R F (2003) The evolution of vertebrate blood coagulation as viewed from a comparison of puffer fish and sea squirt genomes. *Proc Natl Acad Sci USA* 100:7527-7532.
6. Davidson C J, et al. (2003) Molecular evolution of the vertebrate blood coagulation network. *Thromb Haemost* 89:420-428.
7. Rao V S, Swarup S, Kini R M (2003) The nonenzymatic subunit of pseutarin C, a prothrombin activator from eastern brown snake (*Pseudonaja textilis*) venom, shows structural similarity to mammalian coagulation factor V. *Blood* 102:1347-1354.
8. St. Pierre L, et al. (2005) Comparative analysis of prothrombin activators from the venom of Australian elapids. *Mol Biol Evol* 22:1853-1864.
9. Welton R E, Burnell J N (2005) Full length nucleotide sequence of a factor V-like subunit of oscutarin from *Oxyuranus scutellatus scutellatus* (coastal Taipan). *Toxicon* 46:328-336.
10. Sutherland S, Tibballs J (2001) in *Australian Animal Toxins. The Creatures, Their Toxins and Care of the Poisoned Patient*. (Oxford University Press, Melbourne, Australia).
11. Owen W G, Jackson C M (1973) Activation of prothrombin with *Oxyuranus scutellatus scutellatus* (taipan snake) venom. *Thromb Res* 3:705-714.
12. Walker F J, Owen W G, Esmon C T (1980) Characterization of the prothrombin activator from the venom of *Oxyuranus scutellatus scutellatus* (taipan venom). *Biochemistry* 19:1020-1023.
13. Masci P P, Whitaker A N, de Jersey J (1988) Purification and characterization of a prothrombin activator from the venom of the Australian brown snake, *Pseudonaja textilis textilis*. *Biochem Int* 17:825-835.
14. Speijer H, Govers-Riemslag J W, Zwaal R F, Rosing J (1986) Prothrombin activation by an activator from the venom of *Oxyuranus scutellatus* (Taipan snake). *J Biol Chem* 261:13258-13267.
15. Rao V S, Kini R M (2002) Pseutarin C, a prothrombin activator from *Pseudonaja textilis* venom: its structural and functional similarity to mammalian coagulation factor Xa-Va complex. *Thromb Haemost* 88:611-619.
16. Rao V S, Swamp S, Kini R M (2004) The catalytic subunit of pseutarin C, a group C prothrombin activator from the venom of *Pseudonaja textilis*, is structrually similar to mammalian blood coagulation factor Xa. *Thromb Haemost* 92:509-521.
17. Toso R, Camire R M (2006) Role of Hirudin-like factor Va heavy chain sequences in prothrombinase function. *J Biol Chem* 281:8773-8779.
18. Mann K G (1976) Prothrombin. *Methods Enzymol* 45:123-156.
19. Pryzdial E L G, Mann K G (1991) The association of coagulation factor Xa and factor Va. *J Biol Chem* 266:8969-8977.
20. Boskovic D S, Giles A R, Nesheim M D (1990) Studies of the role of factor Va in the factor Xa-catalyzed activation of prothrombin, fragment 1 2-prethrombin-2, and dansyl-1-glutamyl-glycyl-1-arginine-meizothrombin in the absence of phospholipid. *J Biol Chem* 265:10497-10505.
21. Esmon C T (2003) The protein C pathway. *Chest* 124:26S-32S.
22. Higgins D L, Mann K G (1983) The interaction of bovine factor V and factor V-derived peptides with phospholipid vesicles. *J Biol Chem* 258:6503-6508.
23. Buddai S K, et al. (2002) Nematode anticoagulant protein c2 reveals a site on factor Xa that is important for macromolecular substrate binding to human prothrombinase. *J Biol Chem* 277:26689-26698.
24. Camire R M, Larson P J, Stafford D W, High K A (2000) Enhanced g-carboxylation of recombinant factor X using a chimeric construct containing the prothrombin propeptide. *Biochemistry* 39:14322-14329.
25. Camire R M (2002) Prothrombinase assembly and S1 site occupation restore the catalytic activity of FXa impaired by mutation at the sodium-binding site. *J Biol Chem* 277:37863-37870.
26. Lundblad R L, Kingdon H S, Mann K G (1976) Thrombin *Methods Enzymol* 45:156-176.
27. Di Scipio R G, Hermodson M A, Yates S G, Davie E W (1977) A comparison of human prothrombin, factor IX (Christmas Factor), factor X (Stuart Factor), and protein S. *Biochemistry* 16:698-706.
28. Stafford W F (1992) Boundry analysis in sedimentation transport experiments: a procedure for obtaining sedimentation coefficient distributions using the time derivative of the concentration profile. *Anal Biochem* 203:295-301.
29. Babul J, Stellwagen E (1969) Measurement of protein concentration with interferences optics. *Anal Biochem* 28:216-221.
30. Horton R M, et al. (1989) Engineering hybrid genes without the use of restriction enzymes: gene splicing by overlap extension. *Gene* 77:61-68.
31. Bevington P R, Robinson K D (1992) in *Data Reduction and Error Analysis for the Physical Sciences*. (McGraw-Hill, New York).
32. Straume M, Johnson M L (1992) Analysis of residuals: criteria for determining goodness-of-fit. *Methods Enzymol* 210:87-105.
33. Krishnaswamy S (1990) Prothrombinase complex assembly: Contributions of protein-protein and protein-membrane interactions toward complex formation. *J Biol Chem* 265:3708-3718.
34. Segal I H (1975) in *Enzyme Kinetics: Behavior and Analysis of Rapid Equilibrium and Steady State Enzyme Systems*. (John Wiley & Sons, Inc., New York).

While certain preferred embodiments of the present invention have been described and specifically exemplified above, it is not intended that the invention be limited to such embodiments. Various modifications may be made to the invention without departing from the scope thereof as set forth in the following claims.

What is claimed is:

1. A method for the treatment of a blood coagulation disorder in a patient in need thereof, comprising administering an effective amount of an activated form of isolated snake factor V (FV) encoded by the nucleic acid having the nucleotide sequence SEQ ID NO: 1 or SEQ ID NO: 2, thereby enhancing clot formation in said patient and ameliorating the symptoms of said blood coagulation disorder.

2. The method of claim 1, for the treatment of hemophilia A.

3. The method of claim 1, for the treatment of hemophilia B.

4. The method of claim 1, wherein said activated form of FV is delivered intravenously or topically.

5. The method of claim 1, wherein said disorder is selected from the group consisting of hemophilia A and B, hemophilia A and B associated with inhibitory antibodies, coagulation factor deficiency, vitamin K epoxide reductase C1 deficiency, gamma-carboxylase deficiency, bleeding associated with trauma, injury, thrombosis, thrombocytopenia, stroke, coagulopathy, disseminated intravascular coagulation (DIC); over-anticoagulation treatment disorders, Bernard Soulier syndrome, Glanzman thromblastemia, and storage pool deficiency.

6. The method of claim 5, wherein said over-anticoagulation treatment disorder results from administration of heparin, low molecular weight heparin, pentasaccharide, warfarin, small molecule antithrombotics, and FXa inhibitors.

7. The method of claim 1, wherein said variant is administered intravenously at least once a day at a dosage between about 10 and 500 µg/kg.

8. The isolated nucleic acid of SEQ ID NO: 2 encoding snake Factor V.

9. The nucleic acid of claim 8 contained in an expression vector.

10. An isolated host cell comprising the nucleic acid of claim 9.

11. The isolated snake Factor V protein encoded by the nucleic acid of SEQ ID NO: 1.

12. The protein of claim 11 contained in a liposome or micelle.

13. A pharmaceutical composition comprising the protein of claim 11 contained in a pharmaceutically acceptable excipient.

* * * * *

UNITED STATES PATENT AND TRADEMARK OFFICE
CERTIFICATE OF CORRECTION

PATENT NO.       : 8,557,762 B2                                          Page 1 of 1
APPLICATION NO. : 13/130378
DATED            : October 15, 2013
INVENTOR(S)      : Camire et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 148 days.

Signed and Sealed this

Fifteenth Day of September, 2015

Michelle K. Lee
*Director of the United States Patent and Trademark Office*

SEQUENCE LISTING

<160> NUMBER OF SEQ ID NOS: 6

<210> SEQ ID NO 1
<211> LENGTH: 4374
<212> TYPE: DNA
<213> ORGANISM: Artificial Sequence
<220> FEATURE:
<223> OTHER INFORMATION: Synthetic Sequence

<400> SEQUENCE: 1

```
atgttcccag gctgcccacg cctctgggtc ctggtggtct tgggcaccag ctgggtaggc       60
tgggggagcc aagggacaga agcggctcag ctcagggagt accatatagc tgctcagctg      120
gaagactggg attacaaccc ccaacctgag gagctatcca gattatcaga gtcagatctt      180
acgtttaaaa aaattgtcta tagagaatat gaactagatt tcaaacaaga gaagccaaga      240
gatgcgctct cagggctcct agggccaaca ctacgtggag aagtgggaga cagcctcata      300
atttatttca agaattttgc tactcagcct gtgagcattc acccgcagag tgccgtgtac      360
aacaaatggt cagaaggttc ttcatattct gatggaacat cagatgtgga agactggat       420
gatgctgtgc ctccaggcca gtcgttcaag tatgtgtgga atatcactgc agaaattggg      480
ccaaagaaag ctgatcctcc ctgtctcact tatgcgtact actcacatgt aaacatggtg      540
cgagacttta attctggtct cattggtgct ttgctgatat gtaagaagg aagcctgaat      600
gcaaatggtt cacaaaaatt cttcaacaga gaatatgtgc tgatgttttc tgtgtttgat      660
gaaagcaaga actggtacag aaagccctca ctacagtaca caattaatgg gtttgccaat      720
ggaacattgc ctgatgttca ggcttgtgct tatgatcata ttagctggca tttgatagga      780
atgagttcca gtcctgagat cttctctgtt cacttcaatg acaaaccttt ggaacaaaac      840
cattacaaag tgtcaaccat caaccttgtc ggaggtgcct cagtaacagc cgacatgtca      900
gtgagcagga caggaaaatg gctaatatct tctctggttg caaagcatct acaagctggg      960
atgtatggtt atctaaatat caaagactgt ggaaatccag atactttaac aagaaagtta     1020
tcctttagag aactgatgaa gattaagaac tgggaatatt tcattgctgc agaagaaatc     1080
acctgggatt atgctccaga aattcctagc agtgttgaca agataccaa agctcagtat     1140
ctggataatt tttcaaattt tattggcaag aaatacaaaa aggcagtttt caggcaatat     1200
gaagacggca atttcactaa accgacctat gccatttggc ccaaagaacg tggaattctg     1260
ggccccgtta tcaaagctaa agtcagagac acagtaacaa ttgtattcaa aaatctggcc     1320
agtcgacctt acagcattta tgtgcatgga gttccgtttt caaaagatgc agaaggagct     1380
atttatcctt cagatcccaa agaatatata actcatggca agcagttga accaggacag     1440
gtctacacat ataaatggac tgtgctggat acagatgaac ctacagtaaa ggattctgag     1500
tgcattacta aattatatca tagtgctgtg gacatgacaa gagatattgc ttcaggactt     1560
attgggccac ttctggtttg taaacacaag gcactcagcg tcaaggggt acagaataaa     1620
gctgatgtgg aacagcatgc agtcttcgca gtgtttgatg aaaacaagag ctggtacttg     1680
gaagacaata tcaagaaata ctgcagcaat ccttccgctg ttaagaaaga tgaccctaaa     1740
ttttacaagt ccaatgttat gtacacactc aatggctatg catcagatag aacagaggtt     1800
ttgagggttt atcagtctga agttgttcaa tggcaccctca ccagcgtagg tacagtggat     1860
gagattgttc cagtacatct ttctggtcac accttcttat ccaagggaaa acatcaagat     1920
attttaaatc ttttccccat gagtggtgaa tctgctactg taacaatgga caatctagga     1980
```

```
acctggcttc tgtcatcatg gggctcctgt gagatgagca atggcatgag attgagattt    2040
ttggatgcca attatgatga tgaagatgag ggaaatgaag aagaggaaga agatgatggt    2100
gatattttg ccgacatttt cattccttca gaagtagtaa aaagaaaga agaggttccc      2160
gtaaattttg taccagaccc agaatcggat gcgctagcaa aagaattagg attaatagat    2220
gacgagggta atccaataat acagccacgc agggaacaga cagaggatga tgaagaacag    2280
ctaatgaaag cttcaatgct tgggcttcga tcatttaagg ggtcagttgc tgaagaagaa    2340
ttgaaacaca cagctctagc tttagaagaa gatgcccatg cttctgatcc tcgaattgac    2400
agtaatagtg cacgtaatcc tgacgacata gctggacgct acctgcgtac tatcaaccgt    2460
ggaaataaaa ggaggtacta cattgcagca gaagaagttt tgtgggacta ctcaccgatc    2520
ggaaaaagtc aagtgagaag tcgcgcagcc aagaccacat tcaaaaaagc tattttccga    2580
agttatcttg atgatacttt ccagacacct agcactggag gagaatatga aaagcatctt    2640
ggtatactgg gtcctatcat tagggctgag gtggatgatg taatcgaaat tcagttcaaa    2700
aatttggcct ctagaccata ctcacttcat gctcatggcc ttctctatga gaaatcttct    2760
gaaggcagaa gctatgatga caagtctcct gaattgttca aaaaggatga tgctatcatg    2820
ccaaatggca catacacata tgtctggcaa gtccctccac ggtcaggacc aacagacaat    2880
acagaaaaat gtaaatcatg gcctattac tctggtgtaa atccggaaaa agatattcac    2940
tctggcttaa ttggacctat tttgatctgc cagaaaggca tgattgacaa gtacaacagg    3000
acaatagaca taagggaatt tgtcttgttt tttatggtct ttgatgagga gaaaagctgg    3060
tactttccaa aatctgacaa aagcacttgt gaagagaaac ttataggagt ccaatctctc    3120
cacacatttc ctgcaattaa tgggatccct tatcagctgc aaggcttgac gatgtacaaa    3180
gatgagaatg tccactggca tttgctgaac atgggtgggc ccaaagatat ccatgttgtt    3240
aattttcatg gtcagacatt cactgaagag ggaagggaag ataatcaact tggagtcctt    3300
cctcttcttc ctggtacatt cgcctccatc aaaatgaaac catccaaaat tggcacatgg    3360
cttttagaaa cagaagttgg tgaaaatcag gaaagaggaa tgcaggctct ctttactgtc    3420
attgacaaag attgtaaatt accaatggga ctggcaagtg gataataca agactcacag    3480
atcagtgctt caggtcatgt tggatattgg gagcctaagc tagcaagact gaataatact    3540
ggaaaatata atgcttggag catcataaag aaggaacatg aacatccgtg gatccagata    3600
gacctacaaa gacaagttgt catcacaggc attcagaccc aaggaaccgt gcaactactg    3660
caacattcgt atactgtgga atattttgtt acctacagcg aagatgggca aaactggatt    3720
acttttaaag gaagacattc cgaaacacaa atgcattttg agggtaattc agatggcacc    3780
acagtaaaag aaaaccacat tgatcctcct attattgcca gatatattag gctgcatcca    3840
accaagttct caacagacc tactttccgc attgaactgt taggttgtga agttgaaggt    3900
tgctcagtgc cattgggaat ggaaagtggg gctatcaaga attcagagat tacagcctct    3960
tcttataaga agacttggtg gagttcatgg gaaccattcc ttgcacgact caatctggaa    4020
ggaggaacaa atgcttggca accagaggta acaacaaag atcaatggtt acaaattgac    4080
ctgcaacacc ttacaaaaat aacaagcata ataactcaag gagccacatc aatgactaca    4140
tcaatgtatg tgaaaacatt ctccatccat tatactgatg acaattcaac atggaagcct    4200
tatttggatg ttcgcacttc catggaaaag gttttcacag gaaatattaa cagtgatggt    4260
catgtcaaac attttttcaa accccctata ttgtccaggt tcattcgtat catccctaaa    4320
acatggaatc aatatattgc actccggata gaattgtttg gttgtgaagt tttt          4374
```

<210> SEQ ID NO 2
<211> LENGTH: 4374
<212> TYPE: DNA
<213> ORGANISM: Artificial Sequence
<220> FEATURE:
<223> OTHER INFORMATION: Synthetic Sequence

<400> SEQUENCE: 2

| | | | | | |
|---|---|---|---|---|---|
| atgttccccg | gctgccccg | cctgtgggtg | ctggtggtgc | tgggcaccag | ctgggtgggc | 60 |
| tggggcagcc | agggcaccga | ggccgcccag | ctgcgcgagt | accacatcgc | cgcccagctg | 120 |
| gaggactggg | actacaaccc | ccagcccgag | gagctgagcc | gcctgagcga | gagcgacctg | 180 |
| accttcaaga | gatcgtgta | ccgcgagtac | gagctggact | tcaagcagga | gaagccccgc | 240 |
| gacgccctga | gcggcctgct | gggccccacc | ctgcgcggcg | aggtgggcga | cagcctgatc | 300 |
| atctacttca | gaacttcgc | cacccagccc | gtgagcatcc | accccagag | cgccgtgtac | 360 |
| aacaagtgga | gcgagggcag | cagctacagc | gacggcacca | gcgacgtgga | gcgcctggac | 420 |
| gacgccgtgc | cccccggcca | gagcttcaag | tacgtgtgga | acatcaccgc | cgagatcggc | 480 |
| cccaagaagg | ccgaccccc | ctgcctgacc | tacgcctact | acagccacgt | gaacatggtg | 540 |
| cgcgacttca | cagcggcct | gatcggcgcc | ctgctgatct | gcaaggaggg | cagcctgaac | 600 |
| gccaacggca | gccagaagtt | cttcaaccgc | gagtacgtgc | tgatgttcag | cgtgttcgac | 660 |
| gagagcaaga | actggtaccg | caagcccagc | ctgcagtaca | ccatcaacgg | cttcgccaac | 720 |
| ggcaccctgc | ccgacgtgca | ggcctgcgcc | tacgaccaca | tcagctggca | cctgatcggc | 780 |
| atgagcagca | gccccgagat | cttcagcgtg | cacttcaacg | ccagaccct | ggagcagaac | 840 |
| cactacaagg | tgagcaccat | caacctggtg | ggcggcgcca | gcgtgaccgc | cgacatgagc | 900 |
| gtgagccgca | ccggcaagtg | gctgatcagc | agcctggtgg | ccaagcacct | gcaggccggc | 960 |
| atgtacggct | acctgaacat | caaggactgc | ggcaaccccg | acaccctgac | ccgcaagctg | 1020 |
| agcttccgcg | agctgatgaa | gatcaagaac | tgggagtact | catcgccgc | cgaggagatc | 1080 |
| acctgggact | acgcccccga | gatccccagc | agcgtggacc | gccgctacaa | ggcccagtac | 1140 |
| ctggacaact | tcagcaactt | catcggcaag | aagtacaaga | aggccgtgtt | ccgccagtac | 1200 |
| gaggacggca | acttcaccaa | gcccaccctac | gccatctggc | ccaaggagcg | cggcatcctg | 1260 |
| ggccccgtga | tcaaggccaa | ggtgcgcgac | accgtgacca | tcgtgttcaa | gaacctggcc | 1320 |
| agccgcccct | acagcatcta | cgtgcacggc | gtgagcgtga | gcaaggacgc | cgagggcgcc | 1380 |
| atctacccca | gcgaccccaa | ggagaacatc | acccacggca | aggccgtgga | gcccggccag | 1440 |
| gtgtacacct | acaagtggac | cgtgctggac | accgacgagc | ccaccgtgaa | ggacagcgag | 1500 |
| tgcatcacca | gctgtacca | gagcgccgtg | gacatgaccc | gcgacatcgc | cagcggcctg | 1560 |
| atcggccccc | tgctggtgtg | caagcacaag | gccctgagcg | tgaagggcgt | gcagaacaag | 1620 |
| gccgacgtgg | agcagcacgc | cgtgttcgcc | gtgttcgacg | agaacaagag | ctggtacctg | 1680 |
| gaggacaaca | tcaagaagta | ctgcagcaac | cccagcgccg | tgaagaagga | cgaccccaag | 1740 |
| ttctacaaga | gcaacgtgat | gtacacccctg | aacggctacg | ccagcgaccg | caccgaggtg | 1800 |
| ctgcgcttcc | accagagcga | ggtggtgcag | tggcacctga | ccagcgtggg | caccgtggac | 1860 |
| gagatcgtgc | ccgtgcacct | gagcggccac | accttcctga | gcaagggcaa | gcaccaggac | 1920 |
| atcctgaacc | tgttccccat | gagcggcgag | agcgccaccg | tgaccatgga | caacctgggc | 1980 |
| acctggctgc | tgagcagctg | gggcagctg | gagatgagca | acggcatgcg | cctgcgcttc | 2040 |
| ctggacgcca | actacgacga | cgaggacgag | ggcaacgagg | aggaggagga | ggacgacggc | 2100 |

| | | |
|---|---|---|
| gacatcttcg ccgacatctt catccccagc gaggtggtga agaagaagga ggaggtgccc | 2160 |
| gtgaacttcg tgcccgaccc cgagagcgac gccctggcca aggagctggg cctgatcgac | 2220 |
| gacgagggca accccatcat ccagccccgc cgcgagcaga ccgaggacga cgaggagcag | 2280 |
| ctgatgaagg ccagcatgct gggcctgcgc agcttcaagg gcagcgtggc cgaggaggag | 2340 |
| ctgaagcaca ccgccctggc cctggaggag gacgcccacg ccagcgaccc ccgcatcgac | 2400 |
| agcaacagcg cccgcaaccc cgacgacatc gccggccgct acctgcgcac catcaaccgc | 2460 |
| ggcaacaagc gccgctacta catcgccgcc gaggaggtgc tgtgggacta cagccccatc | 2520 |
| ggcaagagcc aggtgcgcag ccgcgccgcc aagaccacct tcaagaaggc catcttccgc | 2580 |
| agctacctgg acgacacctt ccagaccccc agcaccggcg gcgagtacga aagcacctg | 2640 |
| ggcatcctgg cccccatcat ccgcgccgag gtggacgacg tgatcgagat ccagttcaag | 2700 |
| aacctggcca gccgccccta cagcctgcac gcccacggcc tgctgtacga aagagcagc | 2760 |
| gagggccgca gctacgacga caagagcccc gagctgttca agaaggacga cgccatcatg | 2820 |
| cccaacggca cctacaccta cgtgtggcag gtgccccccc gcagcggccc caccgacaac | 2880 |
| accgagaagt gcaagagctg ggcctactac agcggcgtga accccgagaa ggacatccac | 2940 |
| agcggcctga tcggccccat cctgatctgc cagaagggca tgatcgacaa gtacaaccgc | 3000 |
| accatcgaca tccgcgagtt cgtgctgttc ttcatggtgt cgacgagga aagagctgg | 3060 |
| tacttcccca agagcgacaa gagcacctgc gaggagaagc tgatcggcgt gcagagcctg | 3120 |
| cacaccttcc ccgccatcaa cggcatcccc taccagctgc agggcctgac catgtacaag | 3180 |
| gacgagaacg tgcactggca cctgctgaac atgggcggcc ccaaggacat ccacgtggtg | 3240 |
| aacttccacg ccagaccctt caccgaggag ggccgcgagg acaaccagct gggcgtgctg | 3300 |
| cccctgctgc ccggcacctt cgccagcatc aagatgaagc ccagcaagat cggcacctgg | 3360 |
| ctgctggaga ccgaggtggg cgagaaccag gagcgcggca tgcaggccct gttcaccgtg | 3420 |
| atcgacaagg actgcaagct gcccatgggc ctggccagcg gcatcatcca ggacagccag | 3480 |
| atcagcgcca gcggccacgt gggctactgg gagcccaagc tggcccgcct gaacaacacc | 3540 |
| ggcaagtaca acgcctggag catcatcaag aaggagcacg agcacccctg gatccagatc | 3600 |
| gacctgcagc gccaggtggt gatcaccggc atccagaccc agggcaccgt gcagctgctg | 3660 |
| cagcacagct acaccgtgga gtacttcgtg acctacagcg aggacggcca gaactggatc | 3720 |
| accttcaagg gccgccacag cgagacccag atgcacttcg agggcaacag cgacggcacc | 3780 |
| accgtgaagg agaaccacat cgaccccccc atcatcgccc gctacatccg cctgcacccc | 3840 |
| accaagttct acaaccgccc caccttccgc atcgagctgc tgggctgcga ggtggagggc | 3900 |
| tgcagcgtgc ccctgggcat ggagagcggc gccatcaaga cagcgagat caccgccagc | 3960 |
| agctacaaga gacctggtg gagcagctgg gagcccttcc tggcccgcct gaacctggag | 4020 |
| ggcggcacca acgcctggca gcccgaggtg aacaacaagg accagtggct gcagatcgac | 4080 |
| ctgcagcacc tgaccaagat caccagcatc atcacccagg gcgccaccag catgaccacc | 4140 |
| agcatgtacg tgaagacctt cagcatccac tacaccgacg acaacagcac ctggaagccc | 4200 |
| tacctggacg tgcgcaccag catggagaag gtgttcaccg gcaacatcaa cagcgacggc | 4260 |
| cacgtgaagc acttcttcaa gccccccatc ctgagccgct tcatccgcat catccccaag | 4320 |
| acctggaacc agtacatcgc cctgcgcatc gagctgttcg gctgcgaggt gttc | 4374 |

<210> SEQ ID NO 3
<211> LENGTH: 6
<212> TYPE: PRT

```
<213> ORGANISM: Artificial Sequence
<220> FEATURE:
<223> OTHER INFORMATION: Synthetic Sequence

<400> SEQUENCE: 3

Ala Gln Leu Arg Glu Tyr
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 4

Thr Ile Asn Arg Gly Asn
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 5

Ile Val Asn Gly Met Asp
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 6

Ala Asn Ser Leu Val
1               5
```